(12) United States Patent
Masson et al.

(10) Patent No.: US 8,982,353 B2
(45) Date of Patent: Mar. 17, 2015

(54) HIGH RESOLUTION SURFACE PLASMON RESONANCE INSTRUMENT USING A DOVE PRISM

(75) Inventors: Jean-François Masson, Montreal (CA); Olivier Bolduc, Deux-Montagnes (CA)

(73) Assignee: Valorisation-Recherche, Limited Partnership, Montreal, QC ( * ) Notice: Subject to any disclaimer, the term of this patent is extended or adjusted under 35 U.S.C. 154(b) by 215 days.

(21) Appl. No.: 13/121,603

(22) PCT Filed: Sep. 30, 2009

(86) PCT No.: PCT/CA2009/001389
§ 371 (c)(1),
(2), (4) Date: Jun. 21, 2011

(87) PCT Pub. No.: WO2010/037227
PCT Pub. Date: Apr. 8, 2010

(65) Prior Publication Data
US 2011/0310383 A1    Dec. 22, 2011

Related U.S. Application Data

(60) Provisional application No. 61/136,743, filed on Sep. 30, 2008.

(51) Int. Cl.
*G01N 21/55* (2014.01)
*G01N 21/552* (2014.01)
*G02B 5/04* (2006.01)

(52) U.S. Cl.
CPC .............. *G01N 21/553* (2013.01); *G02B 5/04* (2013.01)
USPC .......................................... 356/445; 356/322

(58) Field of Classification Search
CPC ... G01N 21/553; G01N 21/554; G01N 21/31; G01N 21/648; G01N 2021/258; G02B 6/1226; B01L 2300/0636; G02F 2203/10
USPC .......... 356/445–448, 300, 319, 322, 326, 327
See application file for complete search history.

(56) References Cited

U.S. PATENT DOCUMENTS

| | | | | |
|---|---|---|---|---|
| 5,485,277 | A * | 1/1996 | Foster | 356/445 |
| 6,570,657 | B1 | 5/2003 | Hoppe et al. | |
| 7,501,288 | B2 * | 3/2009 | Schultz et al. | 436/518 |
| 2003/0219809 | A1 * | 11/2003 | Chen et al. | 435/6 |
| 2005/0244093 | A1 * | 11/2005 | VanWiggeren et al. | 385/12 |
| 2006/0119859 | A1 * | 6/2006 | Su et al. | 356/495 |
| 2006/0210436 | A1 * | 9/2006 | Shenoy | 422/68.1 |

(Continued)

OTHER PUBLICATIONS

Campbell, C.T., Kim, G., "SPR microscopy and its applications to high-throughput analyses of biomolecular binding events and their kinetics", Biomaterials, 28 (2007) 2380.
Green, R.J., Frazier, R.A., Shakesheff, K.M., Davies, M.C., Roberts, C.J., Tendler, S.J.B., "Surface plasmon resonance analysis of dynamic biological interactions with biomaterials", Biomaterials, 21 (2000) 1823.
Mullett, W.M., Lai, E.P.C., Yeung, J.M., "Surface Plasmon Resonance-Based Immunoassays" Methods, 22 (2000) 77.

(Continued)

*Primary Examiner* — Hoa Pham
(74) *Attorney, Agent, or Firm* — Norton Rose Fulbright Canada LLP; Alexandre Daoust

(57) ABSTRACT

A surface plasmon resonance instrument and measuring method, in which a lens collimates light into a light beam, a prism propagates the collimated light beam at a single propagation angle and with internal reflection on a face of the prism, and an analyzer processes the collimated light beam from the prism. The face of the prism is configured to receive a surface plasmon resonance sensor and at least the first lens and the prism are aligned on a single optical axis.

11 Claims, 20 Drawing Sheets

(56) References Cited

U.S. PATENT DOCUMENTS

| | | | |
|---|---|---|---|
| 2006/0255292 A1* | 11/2006 | Ja | 250/484.2 |
| 2007/0046943 A1* | 3/2007 | VanWiggeren et al. | 356/445 |
| 2008/0088845 A1* | 4/2008 | Ke et al. | 356/445 |
| 2009/0086210 A1* | 4/2009 | Ho et al. | 356/445 |
| 2010/0167946 A1* | 7/2010 | Shaw et al. | 506/9 |
| 2011/0116093 A1* | 5/2011 | Liu et al. | 356/432 |
| 2013/0240734 A1* | 9/2013 | Booksh et al. | 250/339.11 |

OTHER PUBLICATIONS

Yuk, J.S., Ha, K.S., "Proteomic applications of surface plasmon resonance biosensors: analysis of protein arrays", Exp. Mol. Med., 37 (2005) 1.

Brockman, J.M., Nelson, B.P., Corn, R.M., "Surface Plasmon Resonance Imaging Measurements of Ultrathin Organic Films", Annu. Rev. Phys. Chem, 51 (2000) 41.

Homola, J., "Present and future of surface plasmon resonance biosensors", Anal. Bioanal. Chem., 377 (2003) 528.

Homola, J., Yee, S.S., Gauglitz, G., "Surface plasmon resonance sensors: review", Sensor. Actuat. B-Chem., 54 (1999) 3.

Phillips, K.S., Cheng, Q.,"Recent advances in surface plasmon resonance based techniques for bioanalysis", Anal. Bioanal. Chem., 387 (2007) 1831.

Lavine, B.K., Westover, D.J., Oxenford, L., Midankar, N., Kaval, N.,"Construction of an inexpensive surface plasmon resonance instrument for use in teaching and research", Microchem J, 86 (2007) 147.

Neuert, G., Kufer, S., Benoit, M., Gaub, H.E., "Modular multichannel surface plasmon spectrometer", Rev. Sci. Instrum., 76 (2005).

Hemmi, A., Nato, T., Aoki, Y., Sato, M., Soh, N., Asano, Y., Akasaka, C., Okutani, S., Ohkubo, S., Kaneki, N., Shimada, K., Eguchi, T., Oinuma, T.,"Development of palm-sized differential plasmon resonance meter based on concept of Sprode", Sensor. Actuat. B-Chem., 108 (2005) 893.

Naimushin, A.N., Soelberg, S.D., Bartholomew, D.U., Elkind, J.L., Furlong, C.E., "A portable surface plasmon resonance (SPR) sensor system with temperature regulation", Sensor. Actuat. B-Chem., 96 (2003) 253.

Akimoto, T., Wada, S., Karube, I.,"A surface plasmon resonance probe without optical fibers as a portable sensing device", Anal. Chim. Acta, 610 (2008) 119.

Gentleman, D.J., Booksh, K.S., "Determining salinity using a multimode fiber optic surface plasmon resonance dip-probe" Talanta, 68 (2006) 504.

Battaglia, T.M., Masson, J.F., Sierks, M.R., Beaudoin, S.P., Rogers, J., Foster, K.N., Holloway, G.A., Booksh, K.S.,"Quantification of Cytokines Involved in Wound Healing Using Surface Plasmon Resonance", Anal. Chem., 77 (2005) 7016.

Masson, J.F., Battaglia, T.M., Khairallah, P., Beaudoin, S., Booksh, K.S.,"Quantitative Measurement of Cardiac Markers in Undiluted Serum", Anal. Chem., 79 (2007) 612.

Masson, J.F., Obando, L., Beaudoin, S., Booksh, K.,"Sensitive and real-time fiber-optic-based surface plasmon resonance sensors for myoglobin and cardiac troponin I", Talanta, 62 (2004) 865.

Slavik, R., Homola, J., Brynda, E., "A miniature fiber optic surface plasmon resonance sensor for fast detection of staphylococcal enterotoxin B", Biosens. Bioelectron., 17 (2002) 591.

Masson, J.F., Kim, Y.C., Obando, L., Peng, W., Booksh, K.S.,"Fiber-Optic Surface Plasmon Resonance Sensors in the Near-Infrared Spectral Region", Appl. Spectrosc., 60 (2006) 1241.

Kim, Y.C., Masson, J.F., Booksh, K.S., "Single-crystal sapphire-fiber optic sensors based on surface plasmon resonance spectroscopy for in situ monitoring", Talanta, 67 (2005) 908.

Kim, Y.C., Banerji, S., Masson, J.F., Peng, W., Booksh, K.S.,"Fiber-optic surface plasmon resonance for vapor phase analyses", Analyst, 130 (2005) 838.

Stemmler, I., Brecht, A., Gauglitz, G.,"Compact surface plasmon resonance-transducers with spectral readout for biosensing applications", Sensor. Actuat. B-Chem., 54 (1999) 98.

Zhao, X.J., Wang, Z., Mu, Y., Zhang, H.Q., Jin, Q.H.,"Simultaneous Multiwavelength Detection Based on Surface Plasmon Resonance Technique", Lab. Robot. Automat., 12 (2000) 104.

Evans, S.D., Allinson, H., Boden, N., Flynn, T.M., Henderson, J.R., "Surface Plasmon Resonance Imaging of Liquid Crystal Anchoring on Patterned Self-Assembled Monolayers", J. Phys. Chem. B, 101 (1997) 2143.

Jordan, C.E., Corn, R.M.,"Surface Plasmon Resonance Imaging Measurements of Electrostatic Biopolymer Adsorption onto Chemically Modified Gold Surfaces", Anal. Chem., 69 (1997) 1449.

Berger, C.E.H., Beumer, T.A.M., Kooyman, R.P.H., Greve, J.,"Surface Plasmon Resonance Multisensing", Anal. Chem., 70 (1998) 703.

Beusink, J.B., Lokate, A.M.C., Besselink, G.A.J., Pruijn, G.J.M., Schasfoort, R.B.M., "Angle-scanning SPR imaging for detection of biomolecular interactions on microarrays", Biosens. Bioelectron., 23 (2008) 839.

Singh, B.K., Hillier, A.C.,"Surface Plasmon Resonance Imaging of Biomolecular Interactions on a Grating-Based Sensor Array", Anal. Chem., 78 (2006) 2009.

Klenkar, G., Valiokas, R., Lundstrom, I., Tinazli, A., Tampe, R., Piehler, J., Liedberg, B., "Piezo Dispensed Microarray of Multivalent Chelating Thiols for Dissecting Complex Protein-Protein Interactions", Anal. Chem., 78 (2006) 3643.

Chinowsky, T.M., Jung, L.S., Yee, S.S.,"Optimal linear data analysis for surface plasmon resonance biosensors", Sensor. Actuat. B-Chem., 54 (1999) 89.

Gentleman, D.J., Obando, L.A., Masson, J.F., Holloway, J.R., Booksh, K.S.,"Calibration of fiber optic based surface plasmon resonance sensors in aqueous systems", Anal. Chim. Acta, 515 (2004) 291.

Johansen, K., Stalberg, R., Lundstrom, I., Liedberg, B.,"Surface plasmon resonance: instrumental resolution using photo diode arrays", Meas. Sci. Tech., 11 (2000) 1630.

Tao, N.J., Boussaad, S., Huang, W.L., Arechabaleta, R.A., D'Agnese, J., "High resolution surface plasmon resonance spectroscopy", Rev. Sci. Instrum., 70 (1999) 4656.

Masson, J.F., Battaglia, T.M., Cramer, J., Beaudoin, S., Sierks, M., Booksh, K.S., "Reduction of nonspecific protein binding on surface plasmon resonance biosensors", Anal. Bioanal. Chem., 386 (2006) 1951.

Livermore, D.M., "b-Lactamases in Laboratory and Clinical Resistance", Clinical Microbiology Reviews, 8 (1995) 557.

Yolken, R.H., Hughes, W.T., Stoppa, P.J., "Rapid diagnosis of infections caused by filactamase-producing bacteria by means of an enzyme radioisotopic assay", The Journal of Pediatrics, 97 (1980) 715.

Wong, C.L et al., "Optical characterization of elastohydrodynamic lubricated (EHL) contacts using surface plasmon resonance (SPR) effect.", Tribology International, Butterworth Scientifist LDT, Guildford, GB, vol. 41, No. 5, Nov. 7, 2007, pp. 356-366.

Thariani, R., "Novel, high-quality surface plasmon resonance microscopy.", Sensors and Actuators B: Chemical: International Journal Devoted to Research and Development of Physical and Chemical Transducers, Elsevier S.A, Switzerland, vol. 130 No. 2, Feb. 21, 2008, pp. 765-770.

Lee H. J. et al., "Quantitative functional analysis of protein complexes on surfaces.", The journal of Physiology, vol. 563, No. 1, Dec. 21, 2004, pp. 61-71.

Yuk J. S. et al., "Analysis of protein arrays with a dual-function SPR biosensor composed of surface plasmon microscopy and SPR spectroscopy based on white light.", Sensors and Actuators B: Chemical: International Journal Devoted to Research and Development of Physical and Chemical Transducers, Elsevier S.A, Switzerland, vol. 129, No. 1, Jul. 26, 2007, pp. 113-119.

Bolduc O. R. et al., "High-Resolution surface plasmon resonance sensors based on a dove prism.", Talanta, Elsevier, Amsterdam, NL, vol. 77, No. 5, Oct. 17, 2008, pp. 1680-1687.

\* cited by examiner

HIGH RESOLUTION SURFACE PLASMON RESONANCE INSTRUMENT USING A DOVE PRISM

FIELD

The present invention relates to a Surface Plasmon Resonance (SPR) instrument.

BACKGROUND

SPR sensing has become a widely used technique for the measurement of biomolecular interactions, quantification of proteins, and measurement of DNA. Briefly, SPR relies on an optical excitation of a charge-density oscillation existing at the interface between a thin metallic film and a dielectric material. Resonance conditions are achieved when the light is in total internal reflection at a wavelength-angle couple matching a wavevector of the Surface Plasmon (SP). Multiple optical configurations can possibly excite SPs.

A popular configuration uses monochromatic light to interrogate an angle of resonance with the SP, commonly known as the Kretschmann configuration. Many commercially successful SPR instruments are based on this Kretschmann optical configuration. However, this technology suffers from drawbacks limiting its use in biomedical applications; such SPR instruments are usually expensive to implement, they cannot be deployed on the field due to size constraint of the optical path, and they are not compatible with biological samples. Thus, in spite of the popularity of the Kretschmann SPR instruments, there still exists a need to develop a SPR instrument combining the high resolution of the angle interrogation configuration with the advantages of an inexpensive and portable instrument.

SPR instruments based on different configurations have been investigated as alternatives to the angle interrogation SPR configuration. Among them, a SPR instrument using a fiber optic as the sensing element is a cost effective alternative to research grade instruments; they are portable and can be adapted to various applications such as salinity sensor, biosensor for wound healing, biosensor for cardiac markers, and biosensor for staphylococcal enterotoxin B. Sensitivity of fiber optic SPR can be improved using near infrared excitation of a micro prism located at the tip of the fiber optic. However, the resolution achieved with fiber optic SPR is limited by the numerical aperture (NA) of the optical fiber required to implement fiber optic SPR. A large numerical aperture (NA=0.39) fiber is used to propagate the SPR-active wavelength-angle couples. However, due to a large number of wavelength-angle couples propagating in the fiber optic and entering in resonance with the SPR surface, the SPR spectrum broadens resulting in a limited resolution characterising this configuration. To minimize this effect, a low numerical aperture (NA=0.12) fiber can be modified with a micro-prism at the distal end thereof to improve the SPR spectrum and increase the accessible range of refractive indices. Using the fiber optic SPR configuration, the resolution is limited to approximately $1.4 \times 10^{-6}$ RIU (Refractive Index Unit). Further reduction of the numerical aperture of the optical fiber can achieve a resolution similar to the angle interrogation SPR configuration (approximately $5 \times 10^{-7}$ RIU). However, current manufacturing techniques do not enable such low numerical aperture.

An alternative to angle interrogation SPR or fiber optic SPR uses a multi-wavelength excitation. This configuration combines elements of the angle interrogation SPR and fiber optic SPR instruments. In a multi-wavelength excitation scheme, collimated white light from an excitation optical fiber is reflected at a single angle and the reflected light is analyzed with a spectrophotometer using a collection optical fiber. Among other factors, the resolution of multi-wavelength SPR is limited by the spectral resolution of the spectrophotometer, which is a function of the grating density. The recent development of a miniature spectrophotometer with high spectral resolution may potentially enable the measurement of the refractive index with high resolution using SPR with a small footprint. In the case of the angle interrogation SPR configuration, the resolution depends on scanning of the incident angle (slow measurement and complex mechanical setup) or on focusing of the incident light beam at the interface between a prism and a thin metallic film (made for example of Au) onto a linear array of photodiodes (precise alignment and lengthy optical path are required for high resolution). Hence, the angle interrogation SPR configuration is not suitable for portability and for an inexpensive design of SPR instrument. A current drawback limiting the use of a multi-wavelength SPR instrument is the precise alignment of the optics at the angle of excitation or the manufacture of a small sensing element.

Increasingly, the need for multiplex arrays is arising for simultaneous multi-analyte detection. Spatially resolved SPR measurements provide a technology for monitoring local changes of refractive index on a surface. Thus, the detection of biomolecular interactions for multiple systems/replicates is possible on a spatially resolved sensing array. SPR imaging, also called SPR microscopy, has been applied for high-throughput analyses of biomolecular binding event. SPR imaging methodology has also been recently optimized by improving resolution, optical coupling, and protein array formation. However, no SPR measurement presents the dual capability of measuring the conventional SPR response and the SPR image of a surface.

BRIEF DESCRIPTION OF THE DRAWINGS

In the appended drawings:

FIG. 2b is a schematic top plan view of the SPR instrument of FIG. 2a;

DETAILED DESCRIPTION

Figure 1:
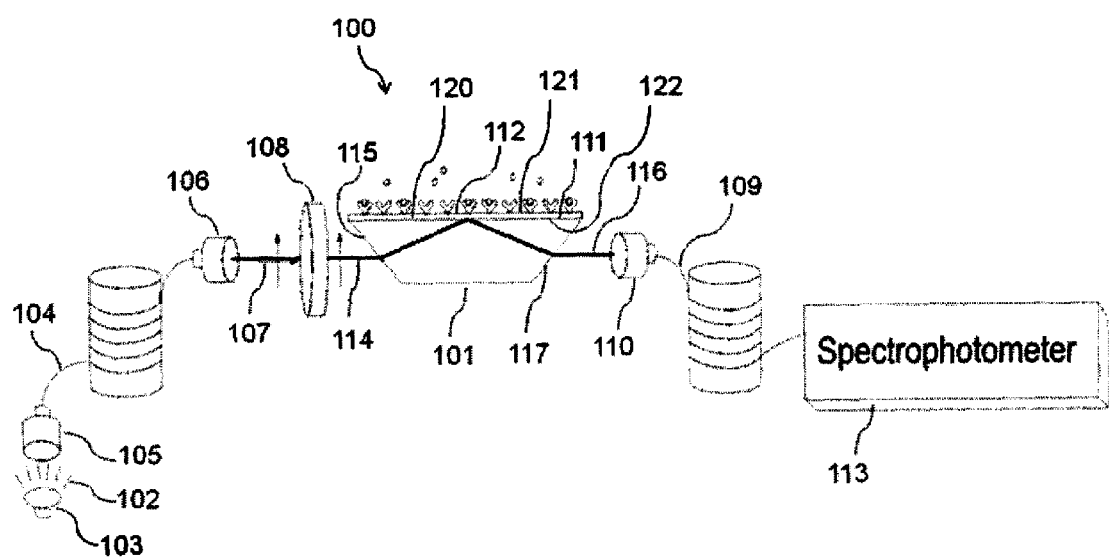
FIG. 1 is a schematic diagram of a SPR instrument using a dove prism, wherein a single axis optical path between an excitation fiber and a collection fiber results in a small-footprint instrument.

According to a first aspect of the present invention, there is provided a surface plasmon resonance instrument, comprising: a first lens for collimating light into a light beam; a prism for propagating the collimated light beam at a single propagation angle and with internal reflection on a face of the prism, wherein the face of the prism is configured to receive a surface plasmon resonance sensor; and an analyzer of the collimated light beam from the prism; wherein at least the first lens and the prism are aligned on a single optical axis.

According to a second aspect of the present invention, there is provided a surface plasmon resonance measuring method, comprising: applying a surface plasmon resonance sensor on a face of a prism; collimating light into a light beam through a first lens; propagating the collimated light beam through the prism at a single propagation angle and with internal reflection on the face of the prism; and analyzing the collimated light beam from the prism; wherein the method further comprises aligning at least the first lens and the prism on a single optical axis.

The foregoing and other objects, advantages and features of the present invention will become more apparent upon reading of the following non restrictive description of illustrative embodiments thereof, given by way of example only with reference to the accompanying drawings.

When integrated to a SPR instrument, multi-wavelength excitation provides a SPR instrument that is portable, inexpensive and exhibiting high resolution. However, as indicated in the foregoing description, a current drawback limiting the use of multi-wavelength SPR instruments is the precise alignment of the optics at the angle of SPR excitation and/or the manufacture of a small sensing element.

The use of a dove prism, or other suitable prism, is advantageous to circumvent these drawbacks. The dove prism inverts the image of a collimated light beam impinging parallel to a long face of the dove prism. The angle of propagation in a BK7 dove prism is 72.8° with respect to the vertical. This angle of propagation of 72.8° results in total internal reflection at the long face of the BK7 dove prism and is active in SPR with an excitation wavelength between 600 nm and 1000 nm depending on the refractive index of the solution being sensed. Hence, a single axis optical path is required to construct the SPR instrument, greatly simplifying the optical setup without loss of spatial or optical resolution. The sensing element can be simply composed of a glass slide coated with Au, onto which fluidics can be mounted for efficient sample delivery. This configuration combines the advantages of portable, inexpensive SPR instrument with the high resolution advantage of biosensing with an angle interrogation configuration SPR instrument.

As also discussed in the foregoing description, no SPR measurement possesses the dual capability of measuring the conventional SPR response and the SPR image of a surface. The use of a SPR configuration with a dove prism can perform both conventional SPR response measurement and SPR imaging with a unique instrumental template.

In the following description, there is described a non-restrictive illustrative embodiment of a SPR instrument based on an optical setup using a BK7 dove prism coupled with fiber optics and a spectrophotometer, for example a miniature spectrophotometer to reduce the size of the SPR instrument. The dynamic range, sensitivity, refractive index resolution, reproducibility and biosensing for β-lactamase are also described. Among the multiple data analysis strategies developed to improve resolution of the SPR signal, the minimum hunting (polynomial fit) and the algorithm (a−b)/(a+b) are used to maximize resolution of the SPR response. Spectral denoising is also performed using singular value decomposition of the spectra to improve the signal-to-noise ratio and increase the resolution of the measured SPR response.

Two configurations of the SPR instrument are possible:

1) A first configuration using a collection fiber optic with a spectrophotometer for multi-wavelength SPR; and 2) A second configuration using a band pass filter and an imaging camera to perform SPR imaging. An image of water droplets on an Au surface of the SPR sensor demonstrates the SPR imaging configuration.

SPR Instrument Using a Dove Prism

The multi-wavelength SPR configuration will be first described.

FIG. 1 is a schematic diagram of a SPR instrument 100 constructed around the combination of wavelength-interrogation fiber optic SPR and total internal reflection in, for example, a BK7 dove prism 101. BK7 identifies a well known optical glass used for fabricating optical components in the visible range. BK7 glass is a relatively hard bor-crown glass, it shows good scratch resistance, has a very low amount of inclusions and is almost bubble-free, and has a high linear optical transmission in the visible range down to 350 nm.

The SPR instrument comprises, as illustrated in FIG. 1, a generator 103 of broadband light 102, for example a halogen lamp. An inverted Shape Memory Alloy (SMA) collimating lens 105 focuses the broadband light 102 from the halogen lamp 103 into a 200 μm-diameter Visible-Near InfraRed (Vis-NIR) fiber optic bundle (excitation fiber optic 104). A SMA collimating lens 106 collimates light from the excitation fiber optic 104 into a collimated light beam 107 having a diameter of about 3 mm. The collimated light beam 107 from the SMA collimating lens 106 is processed through a polarizer 108, for example a p-polarizer, propagates through the BK7 dove prism 101 and is collected by another 200 μm-diameter Vis-NIR fiber optic bundle (collection fiber optic 109) through an inverted SMA collimating lens 110. The collection fiber optic 109 can be identical to the excitation fiber optic 104. The BK7 dove prism 101 comprises a long face 111 to which is applied a SPR sensor 112. The SPR sensor comprises a dielectric layer, for example a glass slide, having one surface covered with a metallic film 121, for example a 48-nm Au film. The surface of the glass slide covered with an Au film is placed opposite to the face 111.

The light exiting the collection fiber optic 109 is supplied to an analyser, for example a spectrophotometer 113 that can be formed by a miniature spectrophotometer. Depending on the Refractive Index (RI) range to be covered, a short spectral range spectrophotometer (550 nm-850 nm) can be used to cover a RI range from 1.32 to 1.39 RIU or a longer spectral range spectrophotometer (550 nm-1100 nm) can be used to cover a RI range from 1.32 to 1.42 RIU.

In the SPR imaging configuration, the collection fiber optic 109 is removed and replaced with an optical band pass filter (610±10 nm) (not shown). The collimated light processed by the optical band pass filter is then analyzed by the analyser. In this case, the analyser may comprise a camera, for example a CCD camera (Andor technology) (not shown). A 50:50 beam splitter can be mounted between the BK7 dove prism 101 and the band pass filter (not shown) for supplying, for example, the collimated light from the lens 110 at the same time to (a) the collection fiber optic 109 and spectrophotometer 113 (SPR wavelength interrogation) and (b) the band pass filter and camera (SPR imaging) on a single platform.

As illustrated in FIG. 1, the optical components 106, 108, 101 and 110 are aligned on a single optical axis. In fact, the above described SPR instrument 100 using, for example, a BK7 dove prism 101 defines a compact and single axis optical path between the excitation fiber optic 104 and the collection fiber optic 109. Accordingly, there is no need for precise alignment of the optics at the angle of SPR excitation.

Also, when the SPR instrument 100 as illustrated in FIG. 1 comprises fiber optic bundles and a miniature spectrophotometer, it is possible to construct a small footprint instrument wherein the optical components occupy a space as small as, for example, 17 cm long, 6.5 cm wide and 17 cm high.

Still referring to FIG. 1, the collimated incident light beam 114 from the polarizer 108 impinges on a face 115 of the BK7 dove prism 101 angular with respect to the single optical axis to propagate through the body of this prism 101 at a single angle of 72.8° with respect to the vertical. At this angle, total internal reflection of the collimated light beam 114 occurs at the long face 111 of the BK7 dove prism 101 which is parallel to the signal optical axis. Also at this angle, surface plasmon resonance on the 48-nm Au film of the SPR sensor 112 is excited at a wavelength of approximately 610 nm with aqueous solutions (FIG. 3). Surface plasmon resonance on the Au film 121 alters the spectral contents of the collimated light beam. When a characteristic or component of a fluid sample contacting the Au film 121 alters surface plasmon resonance on the Au film 121, the spectral contents of the collimated light beam is altered accordingly whereby suitable analysis of the spectral contents of the collimated light beam can detect that characteristic or component of the fluid sample. With this configuration, the SPR instrument 100 combines multi-wavelength excitation with the spectrophotometer 113 to observe the SPR spectrum.

The active SPR area on the sensor 112 is <1 cm$^2$. This active SPR area can be made tunable by providing an iris (not shown) between the excitation fiber optic 104 and the BK7 dove prism 101.

The collimated light beam 116 exits the BK7 dove prism 101 through a face 117 of said prism 101 angular with respect to the single optical axis, and is collected by the collection fiber optic 109 through the inverted SMA collimating lens 110 for analysis by the spectrophotometer 113. As indicated in the foregoing description, the wavelength can range from 550 nm to 850 nm for a short range of accessible refractive index (1.32 to 1.39 RIU) or the wavelength can range from 550 nm to 1100 nm for a broader range of refractive index accessible to the SPR sensor 112 (1.32 to 1.42 RIU). The multi-wavelength SPR instrument 100 has the capacity of simultaneously acquiring a complete wavelength scan of the SPR spectrum, hence allowing for fast acquisition of the SPR spectra. The data can be acquired at a rate of 50 Hz allowing accumulation of 50 spectra composing one data point (1 second time resolution). In comparison, a SPR instrument that scans angles (by physically moving the light source and/or the optics) cannot achieve such time resolution. Otherwise, focusing a light beam on a SPR prism requires a lengthy optical path to achieve optimal spectral resolution. In contrast, using the BK7 dove prism 101 of FIG. 1, it is possible to achieve a compact design without compromising the spectral and temporal resolution. The alignment of the optical components is also much simpler compared to a SPR instrument interrogating multiple angles simultaneously. The BK7 dove prism 101 simply requires the alignment of the optical components along a single optical axis, contrary to a SPR instrument using the angle interrogation configuration which requires focusing of the light with a precise set of angles.

A tunable spectral range is beneficial for different applications. Some applications require high spectral resolution for monitoring the SPR response of low concentration of an analyte with high resolution (for example for biosensing a low protein concentration), while other applications require a large spectral range to monitor changes in refractive index from bulk composition of a solution. With a multi-wavelength SPR configuration, the spectral range of the SPR instrument depends on the grating utilized in the spectrophotometer. For example, a grating with a higher groove density will result in a larger spectral resolution, but a smaller refractive index range accessible to the instrument.

A first implementation uses as spectrophotometer 113, the above mentioned spectrophotometer with the spectral range between 550 nm and 850 nm. This spectrophotometer results in a refractive index range of the SPR instrument 100 between 1.33 and 1.39 RIU (FIG. 3a), which is adequate for most applications with aqueous solutions, such as biosensing. The noise observed on the spectra at wavelengths>750 nm is due to the use, as the light generator 103, of a narrow spectral range LED emitting between 550 nm and 700 nm. A high power LED (Philips lumiled) used as light generator 103 is advantageous, resulting in short integration time (20 ms) for a single acquisition, such that multiple acquisitions are accumulated to compose a single spectrum with a reduced noise on the signal. Hence, kinetic data can be obtained at a fast acquisition rate, with a low noise on the measured spectra.

Figure 3A:
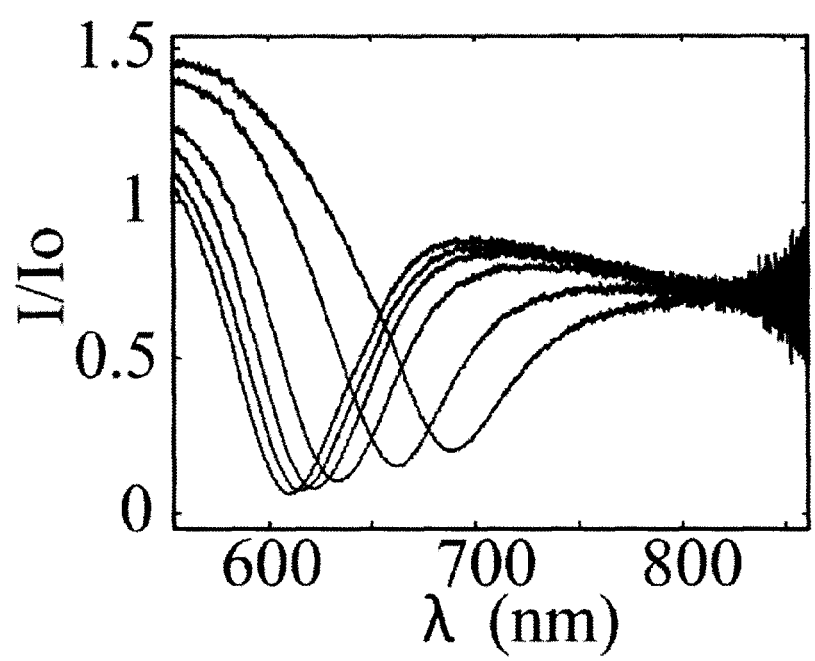
FIG. 3a is a graph showing a SPR spectrum for sucrose solutions with refractive index varying between 1.33 and 1.36 RIU in a short range configuration.
Figure 3B:
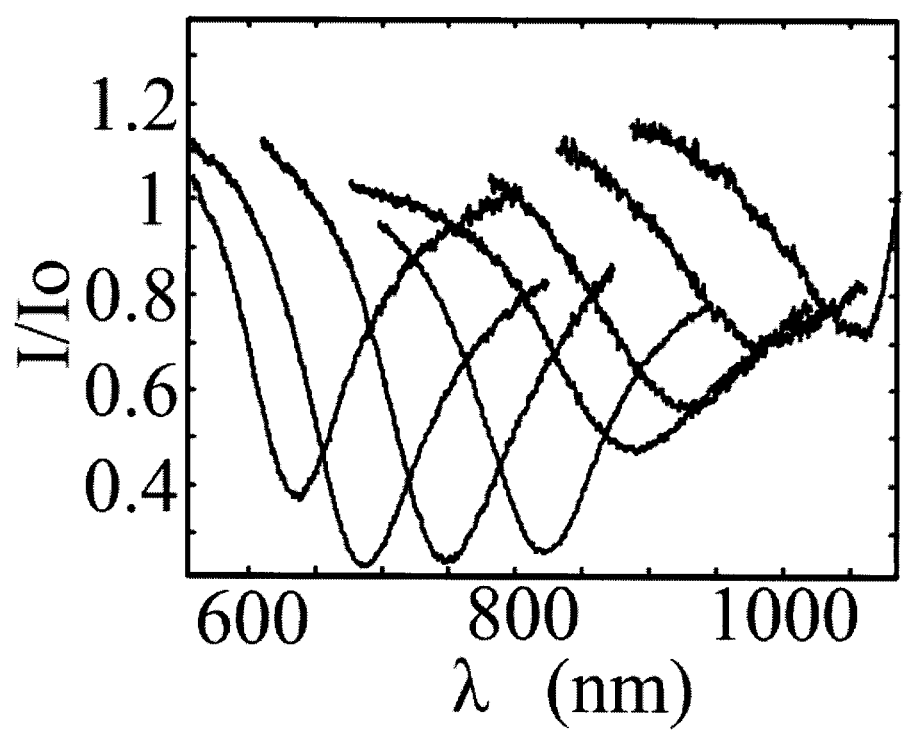
FIG. 3b is a graph showing a SPR spectrum for sucrose solutions with refractive index varying between 1.33 and 1.42 RIU in a long range configuration.

In a second implementation, the SPR spectra are shown using as spectrophotometer 113, the above mentioned spectrophotometer sensitive between 550 nm and 1100 nm (FIG. 3b). This longer spectral range is accessible using a halogen lamp as the light generator 103 and it results in a measurable SPR response for solutions comprised between 1.33 and 1.42 RIU.

Thus, the range of refractive indices accessible to the SPR instrument 100 is tuneable with different spectrophotometers. This multi-wavelength SPR configuration of the SPR instrument 100 results in a single template applicable to different situations.

SPR Sensor

For example, to fabricate the SPR sensor 112, a glass slide 120 of 3"×1" is cleaned using piranha solution (70% $H_2SO_4$: 30% $H_2O_2$) at 80° C. for 90 minutes. The glass slide is then thoroughly rinsed with 18 MΩ water. Thereafter, the glass slide is further cleaned in an ultrasound bath with a 5:1:1 solution of $H_2O:H_2O_2:NH_4OH$ for 60 minutes. Then, the glass slide is thoroughly rinsed with 18 MΩ water and stored in 18 MΩ water until use. The glass slide 120 is air dried undisturbed prior to metallization. Then, to manufacture the SPR sensor 112, a 5 nm-thick adhesion layer of Cr is first deposited on one surface of the slide followed by deposition of the 48 nm Au film 121 on the Cr adhesion layer.

Referring to FIG. 1, the non-metallized surface 122 of the glass slide 120 of the SPR sensor 112 is applied to the long face 111 of the BK7 dove prism 101 through a refractive index matching oil (Refractive Index (RI)=1.5150).

Fluidic Cell

Figure 2A:
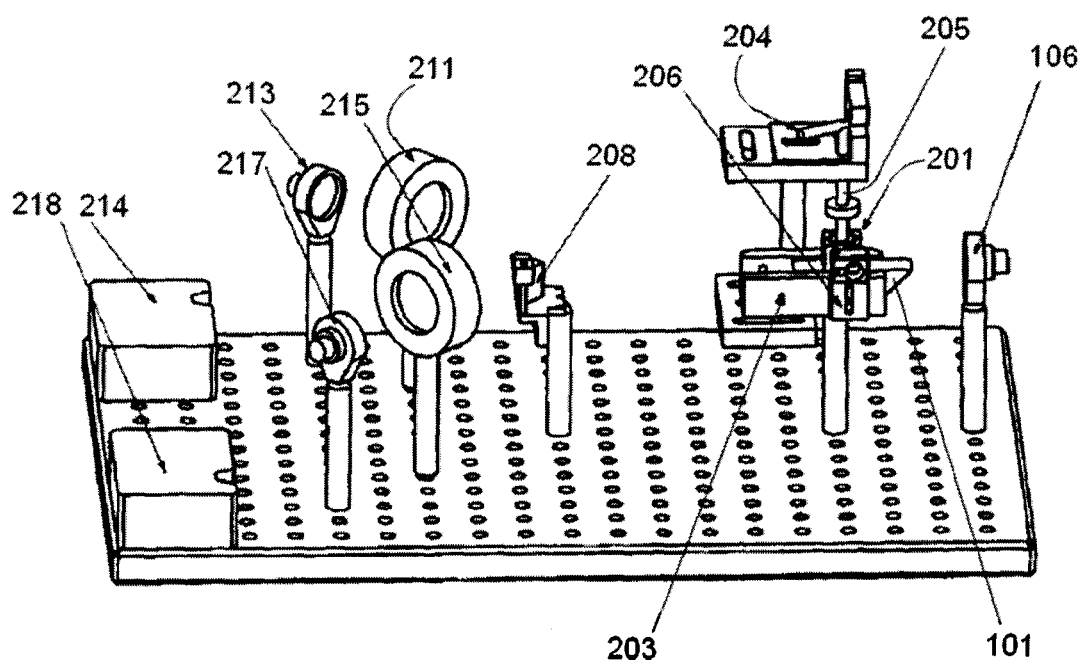
FIG. 2a is a perspective view an auto-referenced or dual channel SPR instrument in which the light beam from the dove prism is split into a s-polarized reference light beam and a p-polarized detection light beam.
Figure 2B:
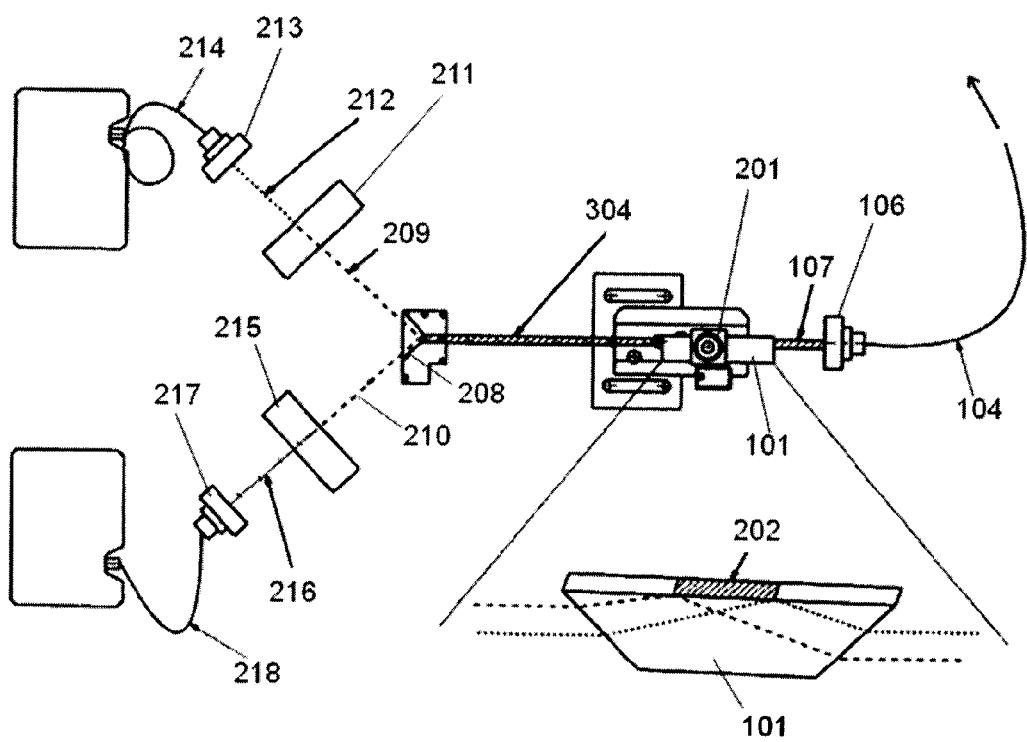

As shown in FIGS. 2a and 2b, a fluidic cell 201 is mounted on the metallised surface 202 (Au film 121) of the glass slide 120. The fluidic cell 201 comprises a body of material, for example a cubic block of Teflon having a bottom face applied to the Au film 121. The bottom face of the cubic block of Teflon is formed with a square recess forming a cell for containing fluid sample to be analysed and destined to contact, for that purpose, the metallized surface 202 (Au film 121). The block of Teflon is also formed with an inlet port and conduit to supply fluid sample to the square recess and an outlet conduit and port to evacuate fluid sample from the square recess. A syringe pump can be used to produce a flow of fluid sample through the square recess in contact with the metallized surface 202. For example, the syringe pump is used to suck fluid sample from a container through the inlet port and conduit, the square recess, and the outlet conduit and port.

For example, the total volume that the square recess can contain is smaller than 100 μL. Also, the flow rate of the liquid sample through the square recess will be typically of the order of 16 μL $s^{-1}$.

Referring to FIGS. 2a and 2b, a mechanism has been designed to hold and apply the fluidic cell 201 to the metallized surface 202 of the glass slide 120. This mechanism comprises a lower support 203 for the dove prism 101. An upper support 204 is mounted above the lower support 203. A removable spring and piston arm 205 is mounted on the upper support 204 and has a free end centered in a recess on the top face of the cubic Teflon block of the fluidic cell 201. The spring applies a pressure on the cubic Teflon block of the fluidic cell 201 both (a) to ensure imperviousness of the volume formed by the square recess in the bottom face of the cubic Teflon block of the fluidic cell 201, and (b) to maintain the vertical position of the fluidic cell 201. A metallic piece 206 mounted to the lower support 203 maintains the horizontal position of the cubic Teflon block of the fluidic cell 201, for example by grasping a nut of a conduit connected to the outlet port of the fluidic cell 201.

Detailed Example of the Fluidic Cell

Figure 8A:
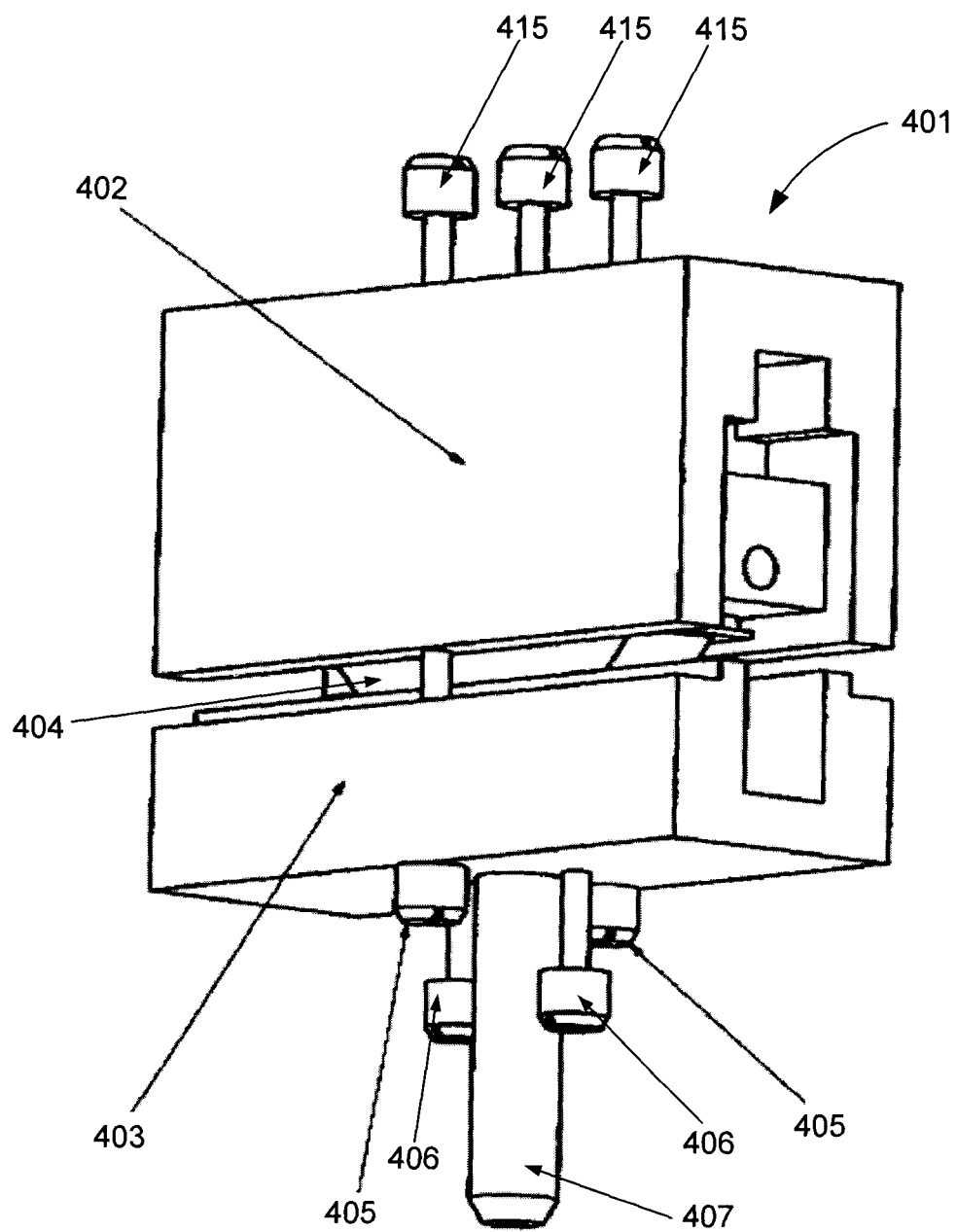
FIG. 8a is a perspective view of an example of a fluidic cell.
Figure 8B:
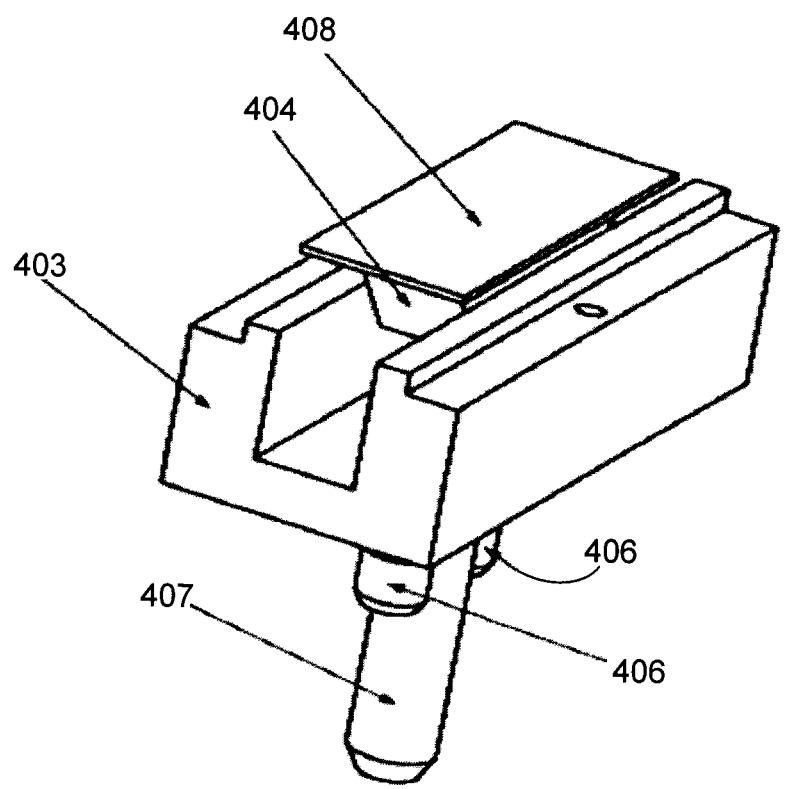
FIG. 8b is a perspective view of the dove prism support of the fluidic cell.
Figure 8C:
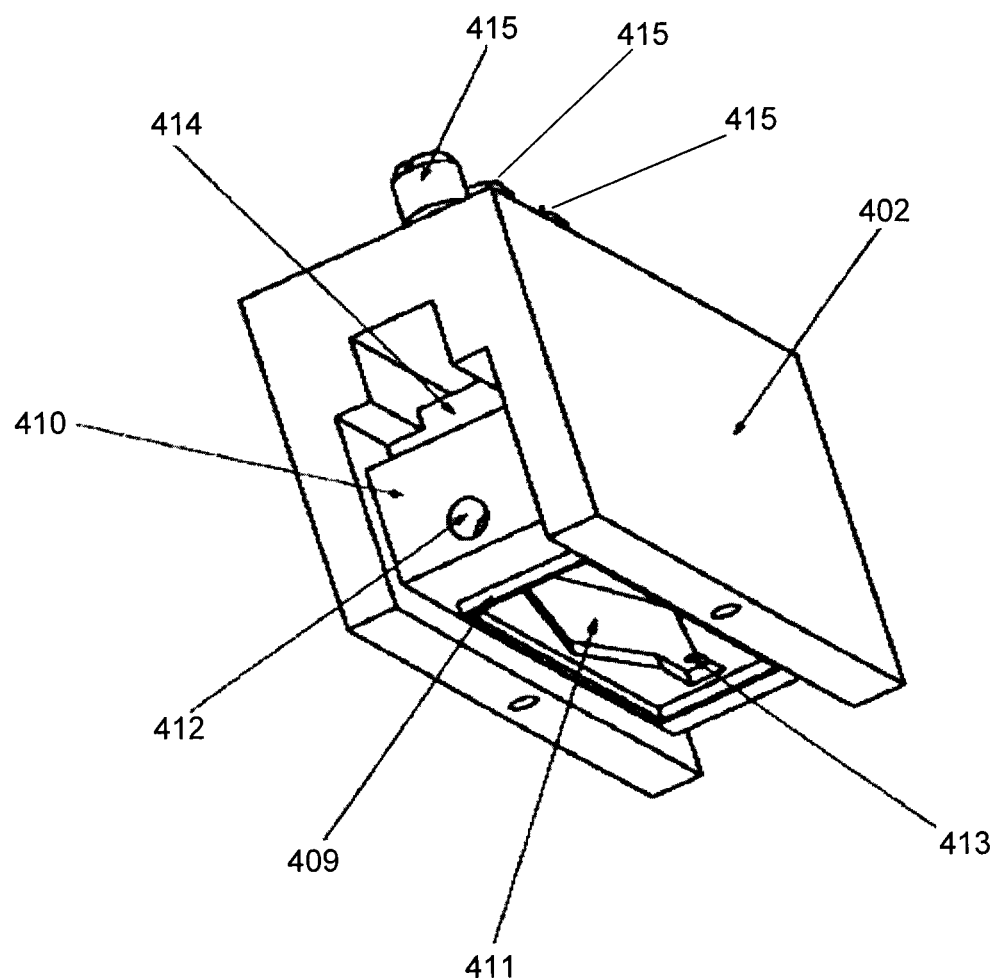
FIG. 8c is a perspective view of the cover of the fluidic cell.

In FIGS. 8a, 8b and 8c, there is shown a detailed example of a fluidic cell 401 which may be used with the SPR instrument 100. The fluidic cell 401 is generally composed of a cover 402 and a dove prism support 403. A dove prism 404 is held in position in the prism support 403 by nylon screws 405 pressing on its sidewall. The dove prism 404 sits on two positioning screws 406 to allow its inclination for an adequate seal of the fluidic cell 401 or for providing a better alignment with the light beam. A metallic post 407 allows the attachment of the fluidic cell 401 to an anti-vibration table. A regular BK7 glass slide 408 coated with gold or silver sits on top of the dove prism 404 using matching oil to avoid any change of refractive index in between. A rubber seal 409 is incorporated into a Teflon block 410 to avoid any unwanted adhesion encloses the fluidic corridor where the solution runs over the sensitive zone. The fluidic corridor is formed by a diamond shaped carve 411 that allows a proper distribution and replacement of the solution. The solution is brought to the fluidic cell 401 through a tube connected to a threaded hole 412 in the Teflon block 410 and exits through hole 413. A metallic pressure plate 414 is screwed on top of the Teflon block 410 to avoid any deformation induced by the three positioning screws 415 that are used to apply pressure on Teflon block 410 to completely seal the fluidic cell 401. The cover 402 of the fluidic cell 401, attached to the prism support 403 via the nylon screws 405, aligns the glass slide 408 and holds the fluidic components in position. This fluidic cell 401 allows the manual and automated replacement of the solution. It is also possible to conduct tests with a constant flow over the sensor or to leave the solution in the cell for static assays.

Miniaturized SPR Instrument

Figure 9:
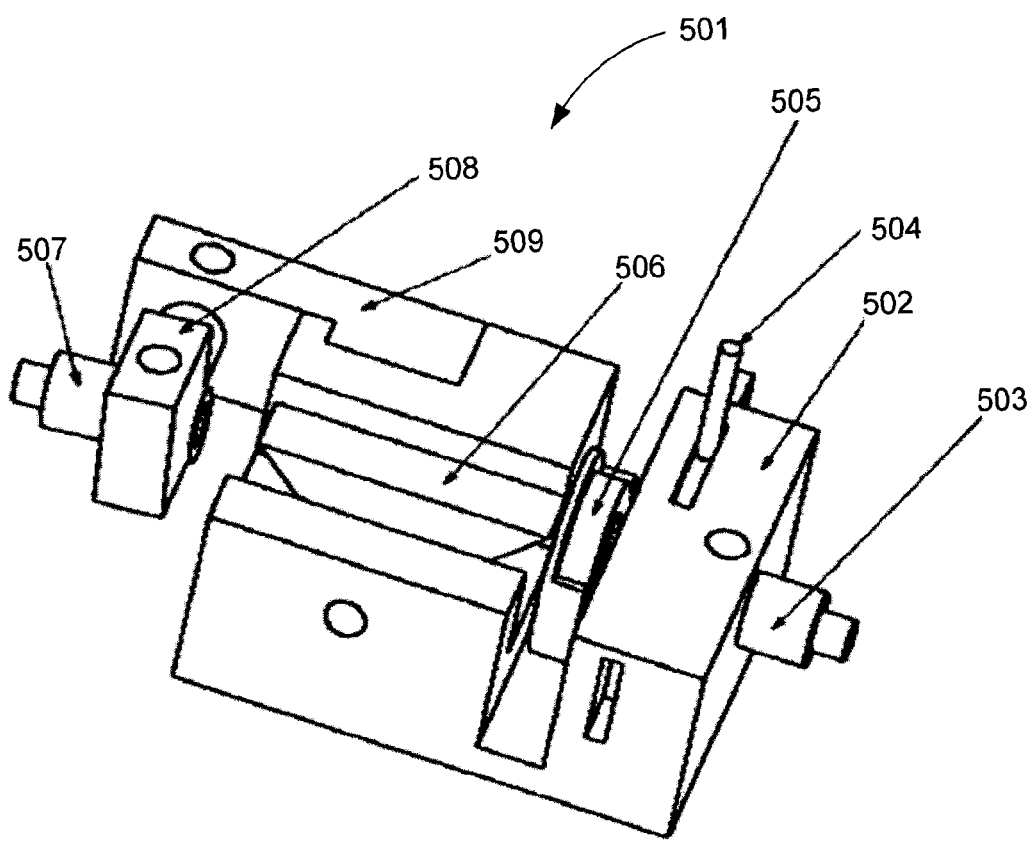
FIG. 9 is a perspective view a miniaturized SPR instrument.

Referring now to FIG. 9, there is shown a miniaturized version of the SPR instrument 100. The miniaturized SPR instrument 501 is generally composed of a small size aluminum mount 502 that integrates all of the components of the SPR instrument 100 while optimizing the distance between its optical components. Light is brought to the miniaturized SPR instrument 501 by an optical fibre and is collimated by a fixed position light emission collimator lens 503. The light beam then passes through one of the two polarizers attached to a polarity controller 504. One of the polarizers corresponds to the "S" polarization while the other corresponds to the "P" polarization. The polarization controller 504 slides to expose one polarizer or the other according to the need of the user. An iris diaphragm 505 limits the area of the light beam that hits the inclined surface of the small size dove prism 506. A glass slide of 22 mm×22 mm coated with gold or silver placed on the dove prism 506 using matching oil acts as a sensor. A nylon screw holds the dove prism 506 in place by applying pressure on its sidewall. A collecting lens 507 is mounted on an angular adjustable light collector holder 508 to allow its rotation. The light collector holder 508 can be moved sideways by sliding it in a hole in the height adjustment slider 509 that moves up and down by sliding in a groove. The two lenses 503 and 507, the holder 508 and the slider 509 are held in position with nylon screws. The total size of the miniaturized SPR instrument 501 is 60 mm×75 mm×30 mm, which makes it fully portable allowing its use directly onsite. It is to be understood, however, that the given dimensions may vary. It is also to be understood that a fluidic cell may be added to the miniaturized SPR instrument 501.

Auto-Referenced or Dual Channel SPR Instrument

As described herein above with reference to FIG. 1, the SPR instrument comprises a SMA collimating lens 106 to collimate light from the excitation fiber optic 104 into a collimated light beam 107. The collimated light beam 107 from the SMA collimating lens 106 propagates through the BK7 dove prism 101 and is collected by a beam splitter 208 comprising, for example, of a right angle prism. The beam splitter 203 separates the collected light beam in two distinct light beams 209 and 210. The first light beam 209 is processed through a s-polarizer 211 to produce a s-polarized reference light beam 212 transmitted to the analyser (not shown) through a SMA collimating lens 213 and a collection fiber optic 214. The second light beam 210 is processed through a p-polarizer 215 to produce a p-polarized detection light beam 216 transmitted to the analyser (not shown) through a SMA collimating lens 217 and a collection fiber optic 218. Therefore, light is separated in two distinct light beams, one used as a s-polarized reference and the other as a p-polarized detection light beam. In this manner, the reference is acquired in real time to minimise deviations.

The configuration and concept of FIGS. 2a and 2b can also be used to measure two regions of the metallized surface 202 of the glass slide 120 of the SPR sensor 112. This results in a SPR instrument with dual measurement channels.

Calibration of the SPR Sensor

The SPR sensor 112 is calibrated to determine its sensitivity to refractive index within the biological realm of refractive indices. The measurement of the SPR response from solutions of varying refractive indices calibrates the SPR sensor 112 for bulk refractive index changes.

For example, for that purpose, sucrose solutions with concentrations ranging from 0% w/w to 50% w/w are prepared in water to cover the range of refractive indices between 1.33 and 1.42 RIU. Thereafter, the solutions are successively exposed to the SPR sensor 112 using the syringe pump and the fluidic cell 201. Data analysis can be performed by the spectrophotometer 113 using two methodologies: minimum hunting [Gentleman, D. J., Obando, L. A., Masson, J. F., Holloway, J. R., Booksh, K. S., Anal. Chim. Acta, 515 (2004) 291] and a (a−b)/(a+b) algorithm around the minimum reflectance of the SPR spectrum [Tao, N. J., Boussaad, S., Huang, W. L., Arechabaleta, R. A., D'Agnese, J., Rev. Sci. Instrum., 70 (1999) 4656]. Singular Value Decomposition (SVD) of the SPR spectra and reconstruction of the SPR spectra using the first three components is performed to optimize the signal-to-noise ratio. With both data analysis methodologies, an Ordinary Linear Least Squares (OLLS) regression model is used to calibrate the SPR sensor 112.

FIGS. 3a and 3b show the SPR spectra for the above first and second implementations, respectively, with sucrose solutions of increasing concentration, thus of increasing refractive index. A refractometer with an accuracy of $1\times10^{-5}$ RIU is used to accurately measure the refractive index of the sucrose solutions. Sucrose solutions are an appropriate model for refractive index calibration, as sucrose does not interact with the Au film of the SPR sensor 112. Hence, the response measured with the SPR sensor 112 results uniquely from the refractive index of bulk solution and no contribution is observed from the accumulation of molecules at the surface. Thereby, the sensitivity of the SPR instrument 100 using the BK7 dove prism 101 is measured at 1765±100 nm/RIU. A calibration curve for SPR sensors is non linear for large refractive index changes, as the refractive index sensitivity increases for solutions of higher refractive index. Therefore, the above measured sensitivity is only valid for the biologically relevant range of refractive indices between 1.33 and 1.35 RIU. The error is for two standard deviations on the regression, calculated using Ordinary Linear Least Square (OLLS) regression.

A non-limitative example related to detection of β-Lactamase using the SPR instrument 100 of FIG. 1 will be described.

Detection of β-Lactamase

A monolayer of the N-hydroxysuccinimide ester of the 16-mercaptohexadecanoic acid (NHS-MHA) is formed by contact of the bare Au film surface of the glass slide 202 of the SPR sensor 112 with a 5 mM solution of NHS-MHA overnight. For example, NHS-MHA can be prepared according the procedure published in Reference [Masson, J. F., Battaglia, T. M., Khairallah, P., Beaudoin, S., Booksh, K. S., Anal. Chem., 79 (2007) 612]. Following a thorough rinse of the NHS-MHA monolayer with ethanol and thereafter with Phosphate Buffered Saline (PBS), the metallized Au surface of the SPR sensor 112 is reacted with anti-β-lactamase (QED Bioscience inc.) prepared at 37 µg/mL in refrigerated PBS pH 7.4. The reaction is carried out overnight in a 4° C. environment to minimize antibody degradation. Thereafter, the samples are rinsed with PBS and reacted for 10 minutes in a 1 M aqueous solution of ethanolamine hydrochloride adjusted at a pH of 8.5 with 10 M NaOH. The slide 120 is then stored in PBS at 4° C. for at least 60 minutes prior to use.

A solution at 700 nM of β-lactamase is prepared in PBS at 4° C. by the dilution of a stock solution. This solution is kept at 4° C. until 20 minutes prior to use, and is then equilibrated at room temperature for the analyses. The following measurements were performed without the use of a flow cell. A SPR sensor 112 with the β-lactamase specific monolayer is placed onto the long face 111 of the BK7 dove prism 101 of the SPR instrument 100 and PBS at room temperature is placed on the SPR sensor 112 for 10 minutes in order to stabilize the SPR sensor 112. A spectral reference (S-polarized light) is acquired immediately before the real-time measurement is started. PBS is measured for 5 minutes to acquire a baseline response and is thereafter replaced with the β-lactamase solution for 20 minutes. Finally, the PBS sensor 112 is placed again in PBS for 5 minutes verifying if the binding between the anti-β-lactamase and β-lactamase is reversible.

Data Analysis Methodologies

Figure 4:
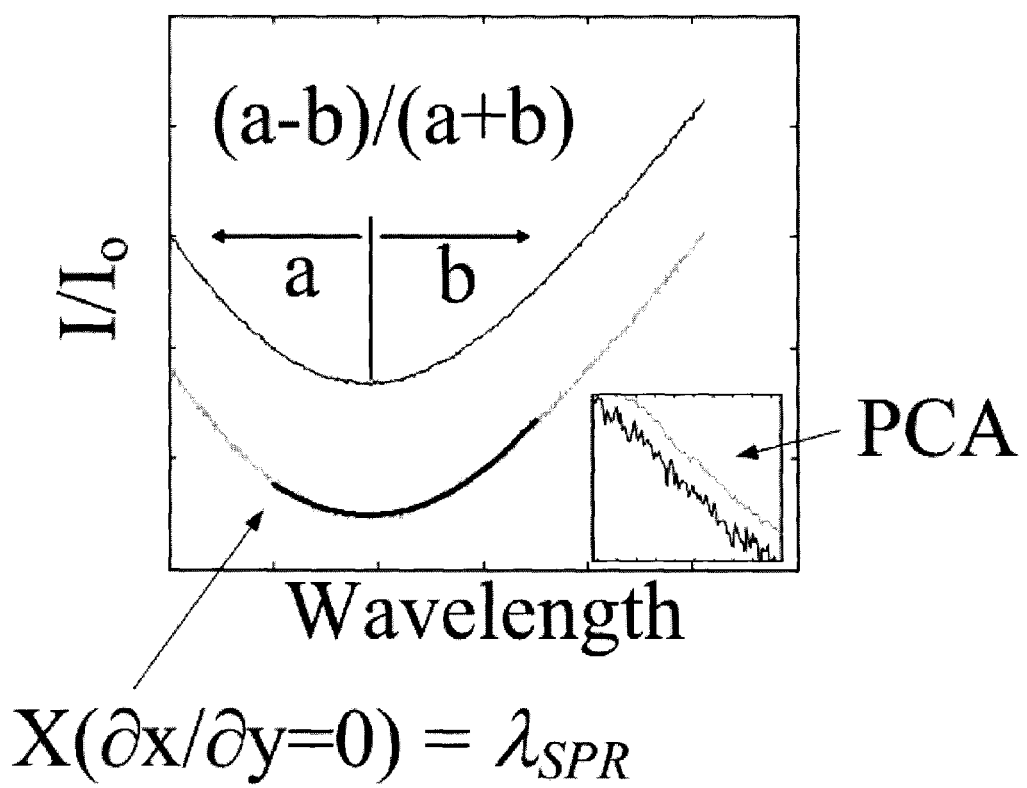
FIG. 4 is a graph showing data analysis of SPR spectra using minimum hunting ($\lambda_{SPR}$) and with the (a−b)/(a+b) algorithm, wherein singular value decomposition (SVD) and reconstitution with the first few components containing the chemical information is used to reduce the noise on the spectra.

The SPR sensor 112 responds to refractive indices with a shift of the wavelength at which the SPR phenomena occurs. Therefore, the data processing methodology used for the determination of the refractive index change will be accurate and sensitive to small changes of spectral position, contrary to the intensity in most spectroscopic applications. Moreover, the noise of the measured response will also be minimized. It is common to use a minimum finding algorithm by mathematically fitting a second order polynomial to the SPR spectra and determining the minimum from the zero of the derivative of the second order polynomial (FIG. 4). Otherwise, an algorithm calculating the difference between the intensity of the branches around a set wavelength (λo), divided by the sum of the intensity for both branches results in a measurement of the position of the SPR response (FIG. 4). Hence, the algorithm (a−b)/(a+b), where a is the sum of the branch for λ<λo, while b is the sum of the branch for λ>λo, is sensitive to minute changes of the position of the SPR response. This algorithm is applied to accurately measure the topography with an atomic force microscope. In order to decrease the noise on the SPR spectra, a singular value decomposition of the SPR spectra into its principal components, followed by the reconstitution of the spectrum with the first few components containing the chemical information reduces the noise. In this case, the reconstitution of the SPR spectra with the first three principal components results in no loss of chemical information.

Figure 5A:
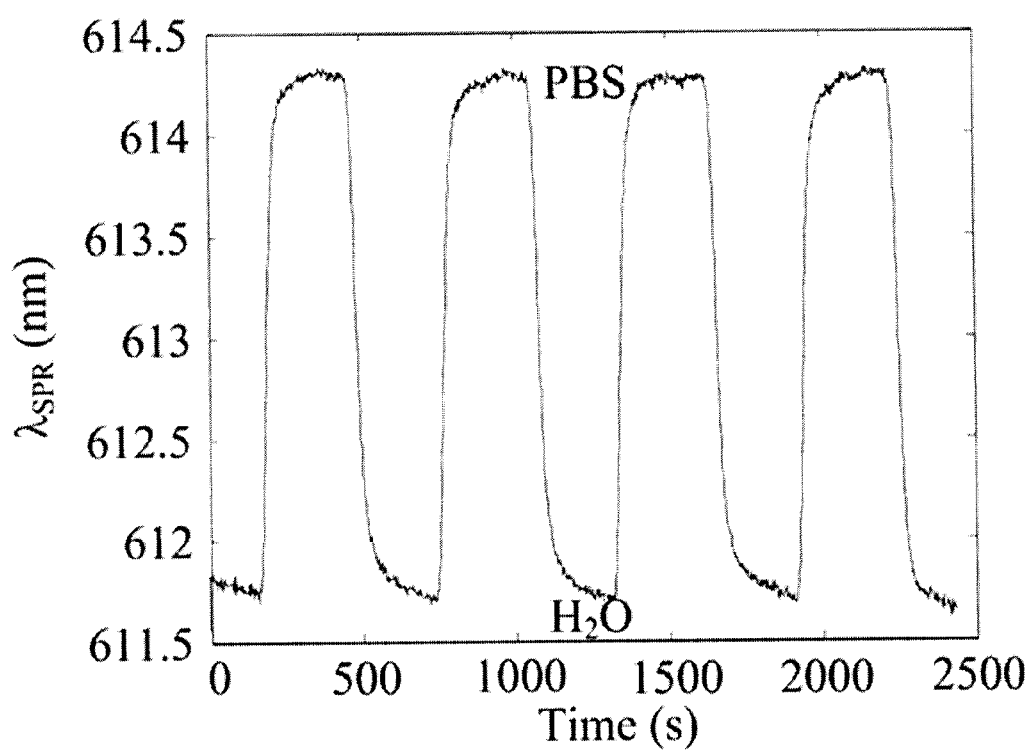
FIG. 5a is a graph showing repeated measurement of Phosphate Buffered Saline (PBS, 1.33498 RIU) and water (1.33287 RIU)
Figure 5B:
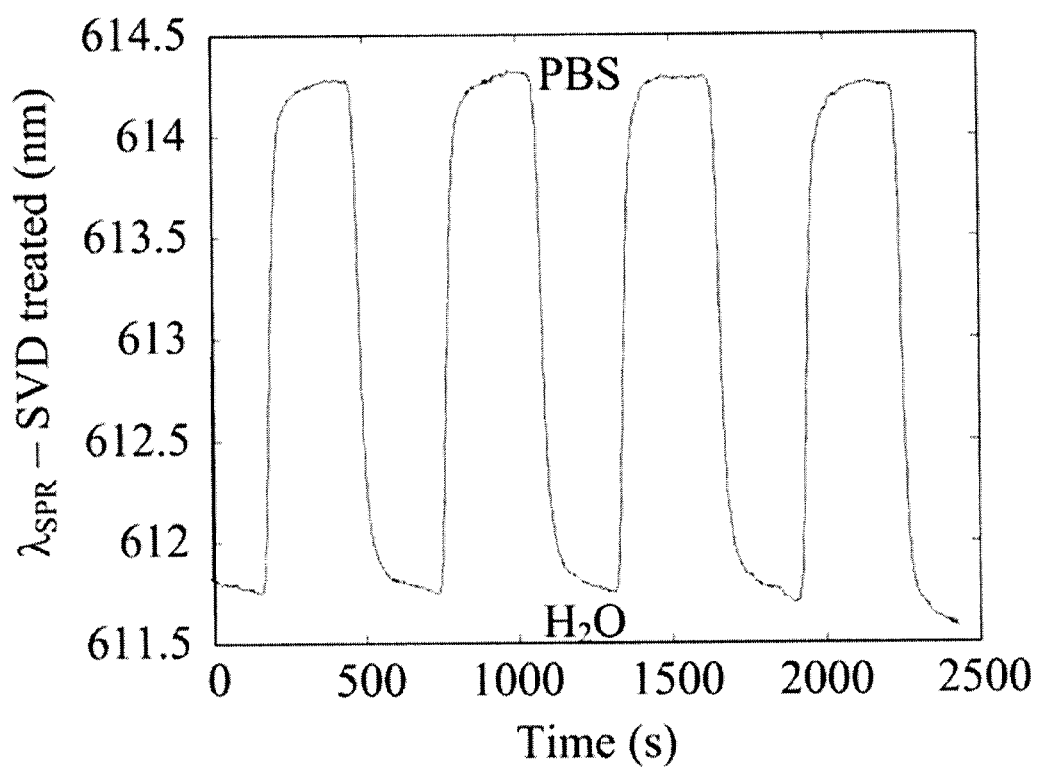
FIG. 5b is a graph showing data analysis using the minimum hunting procedure singular value decomposition of the SPR spectra, reconstitution using the first three components followed by the minimum hunting procedure.
Figure 5C:
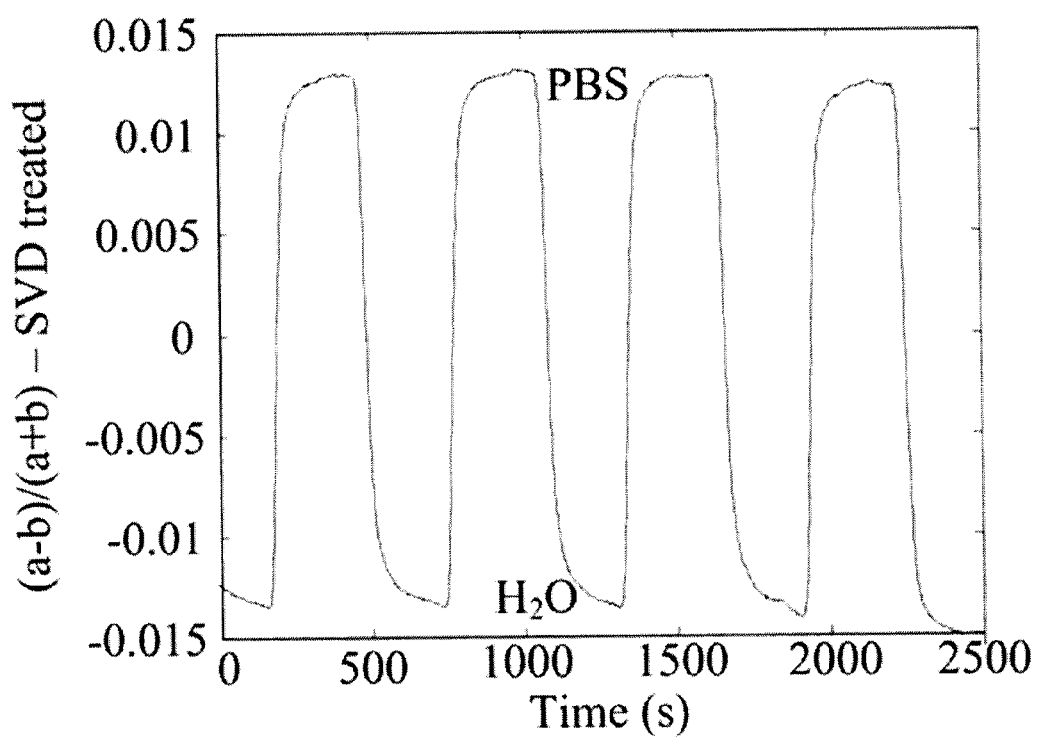
FIG. 5c is a graph showing identical singular value decomposition processing as FIG. 5b, however using the (a−b)/(a+b) algorithm.

As described herein above, the fluidic cell 201 is designed to deliver samples to the SPR sensor 112 using the syringe pump. The syringe pump has a variable flow rate between 0.5 mL/min (8.3 µL/s) to 6.5 mL/min (108 µL/s). The results presented thereafter were obtained at 16 µL/s. To measure the reproducibility of the SPR measurement, the SPR sensor 112 is consecutively exposed for 5 minutes to 18 MO water and then for another 5 minutes to PBS, for a total of four cycles (FIG. 5a). The SPR response is reproducible at a wavelength shift of 2.470±0.011 nm between PBS (RI=1.33498 at 20.00° C.) and water (RI=1.33316 at 20.00° C.) using the minimum hunting data analysis (FIG. 5b). Singular value decomposition of the raw SPR spectra and reconstituting of the SPR spectra with the first three components results in a wavelength shift of 2.482±0.021 nm. The errors reported are for two standard deviations of the mean SPR response. Thus, it is observed that denoising SPR spectra with singular value decomposition and reconstituting them with the first three components do not alter the SPR response. Using the algorithm (a−b)/(a+b) and singular value decomposition (FIG. 5c) denoising yields a response of 0.0257±0.0002 (unitless). The reproducibility of the fluidic cell 201 is better than 1% variation (n=4) with each data analysis methodology.

A significant decrease of the noise on the SPR response is observed from denoising the raw SPR spectra with singular value decomposition. A further decrease of the noise on the SPR spectra is observed for data processing using the (a−b)/(a+b) algorithm. The continuous measurement of the SPR response for a water sample with the fluidic cell 201 is used to calculate the resolution for each data analysis methodologies (Table 1).

TABLE 1

Comparison of data analysis methodologies for flow cell stability and β-lactamase biosensing

|  | Minimum hunting | (a − b)/(a + b) |
|---|---|---|
| | Refractive index resolution | |
| raw data | $3 \times 10^{-6}$ RIU | $9 \times 10^{-7}$ RIU |
| SVD | $1 \times 10^{-6}$ RIU | $1.5 \times 10^{-7}$ RIU |
| | β-lactamase response (700 nM) | |
| raw data | 0.17 ± 0.03 nm | $(6.4 \pm 0.8) \times 10^{-4}$ |
| SVD | 0.127 ± 0.005 nm | $(4.05 \pm 0.15) \times 10^{-4}$ |

Two standard deviations on the mean measurement of the SPR response during a 2-minute exposition to water at a flow rate of 16 μL/s and dividing this value by the sensitivity calculates the resolution. Using minimum hunting without singular value decomposition, the resolution on the refractive index measured is $3 \times 10^{-6}$ RIU. Singular value decomposition denoising the raw spectrum improves the resolution to $1 \times 10^{-6}$ RIU. Therefore, an improvement by a factor of 3 of the resolution is observed when denoising the data using singular value decomposition with minimum hunting. In comparison, the algorithm (a−b)/(a+b) significantly improves the resolution compared to the minimum hunting algorithm. A resolution of $9 \times 10^{-7}$ RIU and $1.5 \times 10^{-7}$ RIU is respectively observed for data processing using the algorithm (a−b)/(a+b) without denoising and with singular value decomposition denoising. Therefore, a greater improvement is observed by denoising the data prior to processing with the algorithm (a−b)/(a+b) compared with the minimum hunting algorithm. This greater improvement on the resolution observed for denoising using the algorithm (a−b)/(a+b) may be due to the methodology of data processing. The main factor limiting the resolution for the minimum hunting procedure is the accuracy of the polynomial fit of the SPR minimum. The random noise on the SPR spectra does not alter significantly the shape of the spectra. Thus, the fit of the second order polynomial for minimum hunting is only slightly improved by denoising. For the algorithm (a−b)/(a+b), the resolution is mainly limited by the random noise on the measurement. In this case, the reduction of the noise from random fluctuations on the spectrum significantly impacts the resolution of the SPR response. This results in a greater reduction of the noise and it improves significantly the resolution of the SPR instrument. The resolution in the $10^{-7}$ RIU range rivals with the best SPR instruments and is adequate for high resolution SPR biosensing. Resolutions were reported for angular interrogation SPR at $5 \times 10^{-7}$ RIU, at $1.4 \times 10^{-6}$ RIU for fiber optic SPR, at approximately $10^{-5}$ RIU for wavelength interrogation SPR, and at $5 \times 10^{-5}$ RIU for intensity measurement SPR (SPR imaging). The significantly improved resolution obtained with the SPR instrument 100 comprising a BK7 dove prism 101 compared to other wavelength interrogation instrument is due to the data processing methodology and to a single angle excitation of the SPR phenomena. Other wavelength interrogation techniques do not impinge the SPR sensor at a unique angle. This results in a broader SPR spectrum and it decreases the resolution of other multi-wavelength SPR instruments.

Figure 5D:
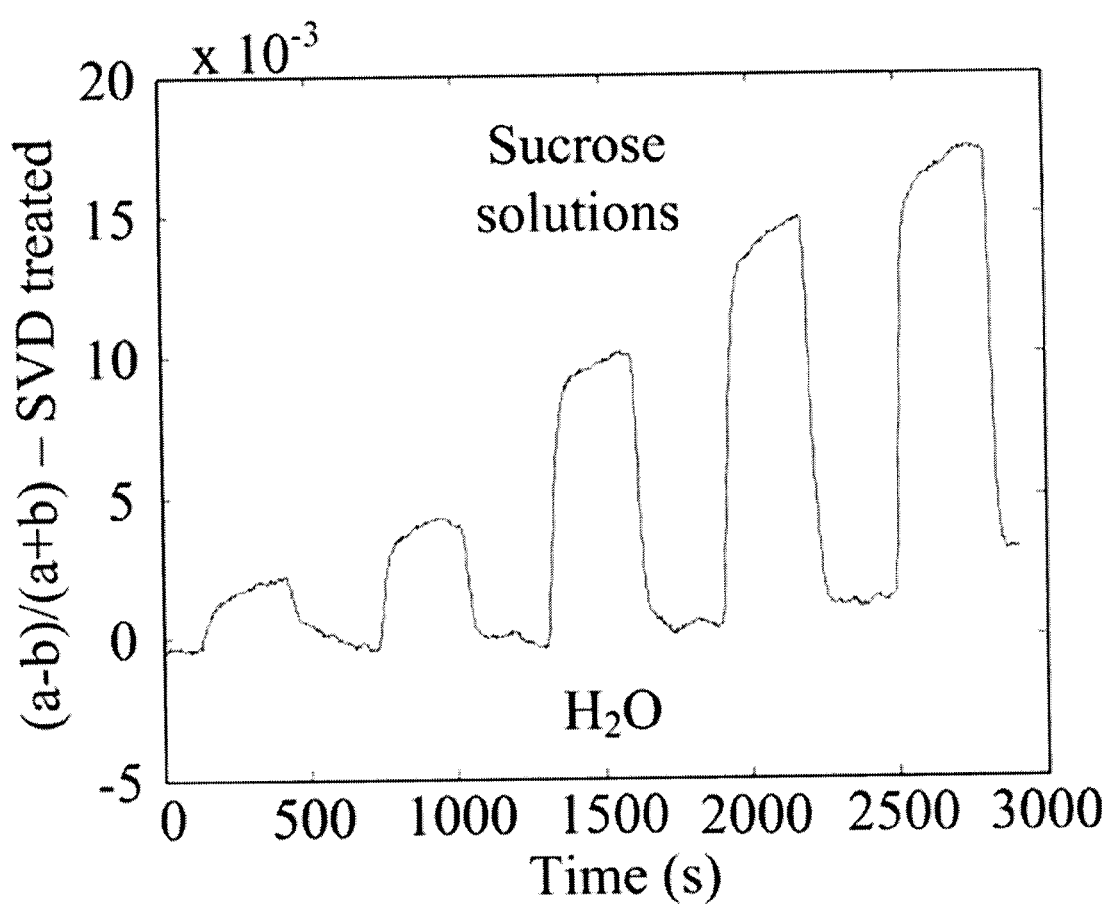
FIG. 5d is a graph showing a calibration curve for sucrose solutions (RI ranges between 1.333 RIU and 1.334 RIU) using a flow cell, Principal Component Analysis (PCA) processing and the (a−b)/(a+b) algorithm.

To exhibit the potential to measure solutions with a small refractive index difference, a calibration curve was constructed for sucrose solutions with a refractive index between 1.333 and 1.334 (FIG. 5d). Therefore, the difference in refractive index between each sucrose solutions is $<2 \times 10^{-4}$ RIU. As can be observed in FIG. 5d, the signal-to-noise ratio on the SPR response does not approach the limit of detection. The SPR signal measured with the algorithm (a−b)/(a+b) shows a linear response to refractive index, due to the short range of the calibration curve. The non-linearity of the SPR calibration is significant for refractive index calibration spanning over differences of >0.02 RIU. The sensitivity to refractive index was measured at 12.5 $RIU^{-1}$ with the algorithm (a−b)/(a+b). The response measured with this data processing algorithm is unitless.

β-Lactamase Biosensing

The SPR instrument is characterized for biosensing with a model biological system. A bioassay for β-lactamase is performed with the immobilization of anti-β-lactamase on a monolayer of N-hydroxysuccinimide ester of 16-mercaptohexadecanoic acid (NHS-MHA). Immobilization of antibodies to a NHS-MHA monolayer has been demonstrated to maximize sensitivity in a direct bioassay format [Masson, J. F., Battaglia, T. M., Cramer, J., Beaudoin, S., Sierks, M., Booksh, K. S., Anal. Bioanal. Chem., 386 (2006) 1951]. β-lactamase is an appropriate biological model system due to its role in the resistance to traditional antibiotics, a commonly occurring problem in patients. The presence of β-lactamase is one of the most common factor in antibiotic resistance. However, the detection technique for antibiotics resistance still relies on standard microbiological methodologies, limiting the time required to perform the assay and the throughput of the assay for antibiotics resistance. Hence, detection of β-lactamase using SPR biosensors would offer improved methodology to quantify β-lactamase compared to actual detection techniques.

Figure 6A:
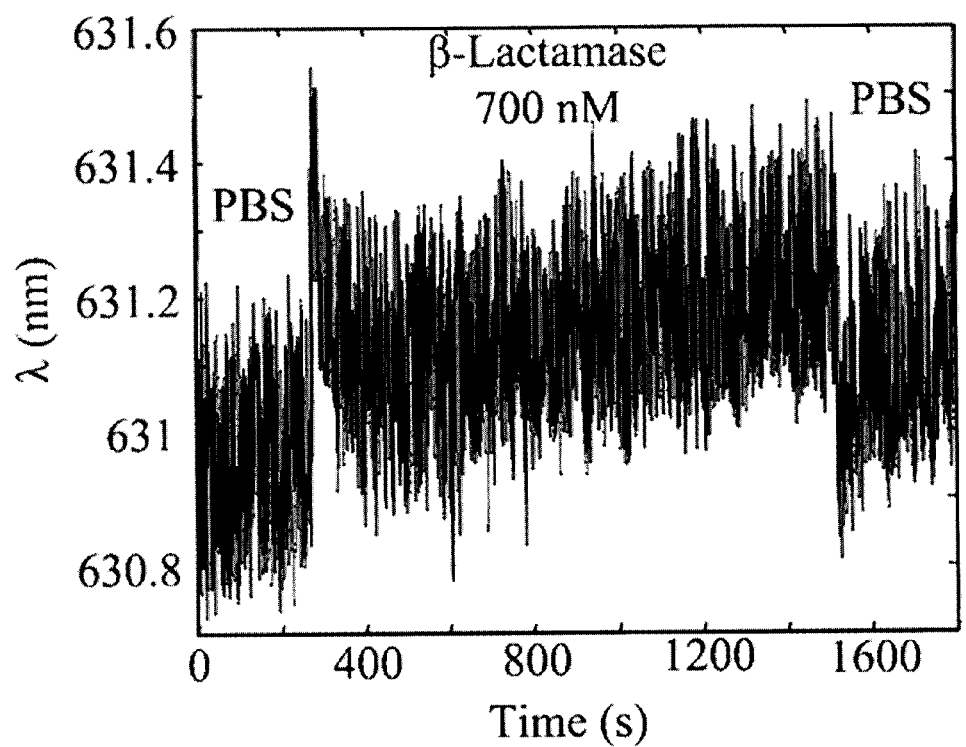
FIG. 6a is a graph showing measurement of β-lactamase in PBS at nM levels using dove prism SPR and minimum hunting algorithm (relative error=21%)
Figure 6B:
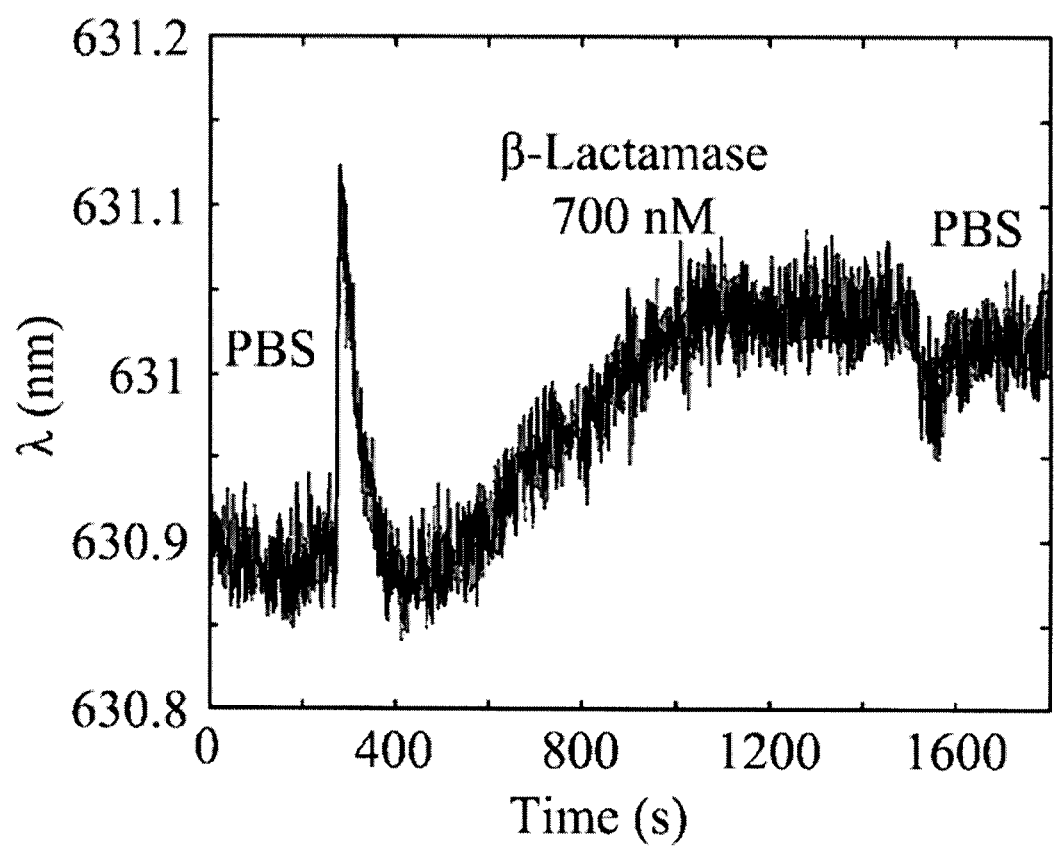
FIG. 6b is a graph showing measurement of β-lactamase in PBS at nM levels using the dove prism SPR and minimum hunting algorithm with singular value decomposition (relative error=3.9%)
Figure 6C:
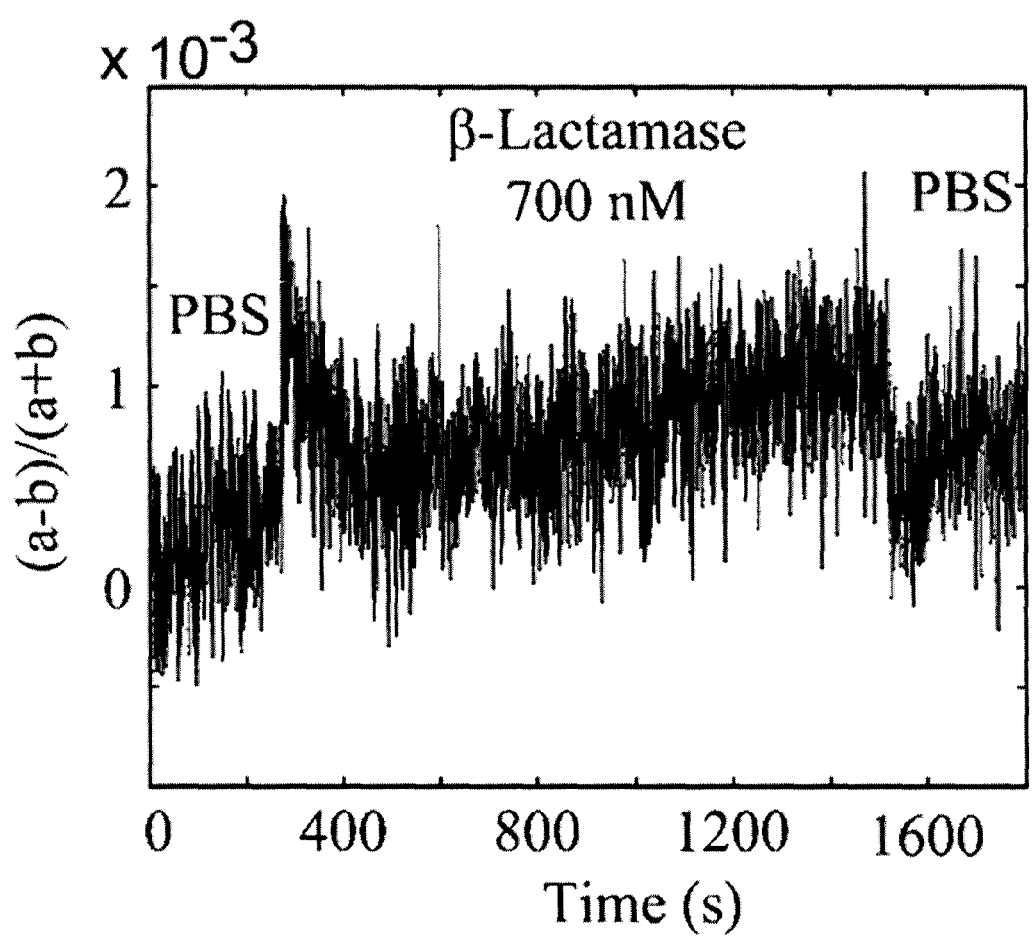
FIG. 6c is a graph showing measurement of β-lactamase in PBS at nM levels using the dove prism SPR and the (a−b)/(a+b) algorithm (relative error=13%)
Figure 6D:
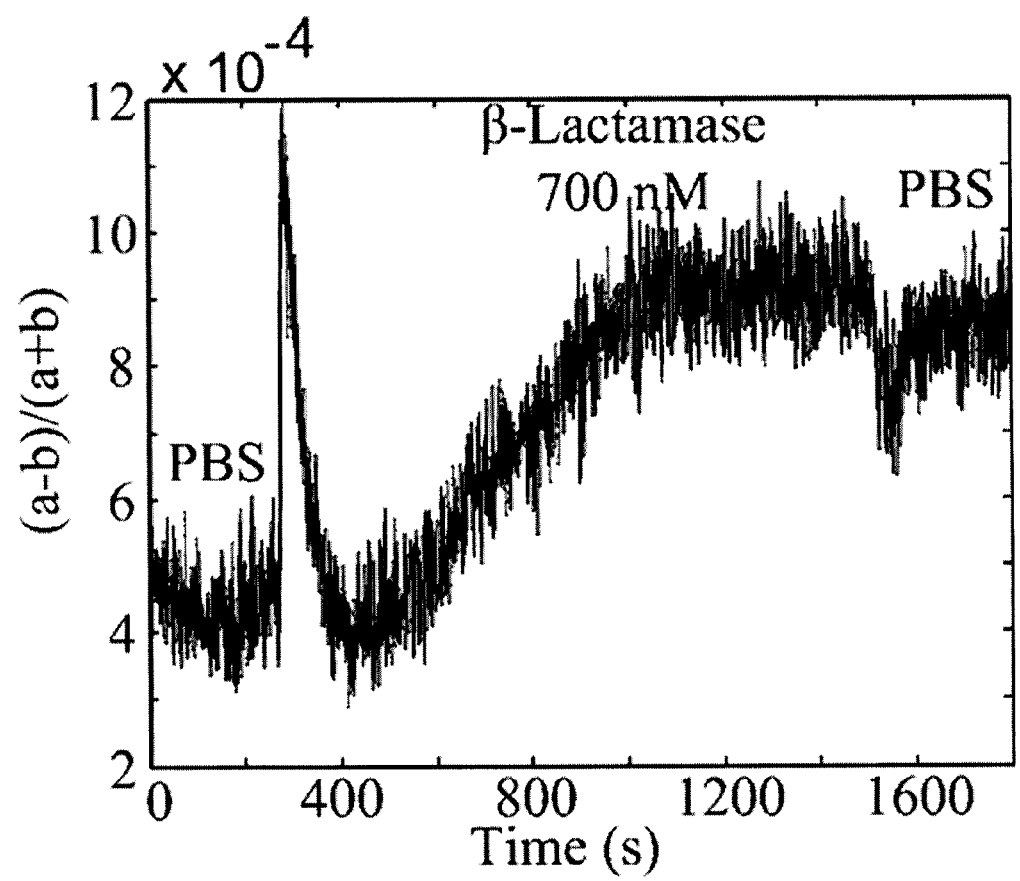
FIG. 6d is a graph showing measurement of β-lactamase in PBS at nM levels using the dove prism SPR and the (a−b)/(a+b) algorithm with singular value decomposition (relative error=3.7%)

The detection of β-lactamase is performed in a PBS solution at nM concentration (FIG. 6a-6b). β-lactamase was measured without the flow cell, in a diffusion limited regime. Each data analysis methodology investigated herein above is used to process data in a comparative study. A significant improvement of the noise level is observed in the response of the β-lactamase biosensor depending of the data analysis methodology. The binding event of β-lactamase is visually undistinguishable from background noise using the minimum hunting algorithm procedure (FIG. 6a). The change of the SPR response between the PBS measured after β-lactamase binding and from the baseline prior to binding of β-lactamase is 0.17±0.03 nm. The error represents two standard deviations on the mean and a relative error of 21%. Denoising data with singular value decomposition significantly improves the signal-to-noise ratio (FIG. 6b). The β-lactamase binding curve is clearly observed following denoising of the SPR spectra analyzed with the minimum hunting algorithm. The change of the SPR response is then 0.127±0.005 nm, resulting in a significantly-reduced relative error at 3.9%. The algorithm (a−b)/(a+b) reduces the noise level on the binding curve of β-lactamase compared to the minimum hunting procedure (FIG. 6c). The response measured is $(6.4\pm0.8)\times10^{-4}$ (unitless) with the algorithm (a−b)/(a+b). Hence, the relative error is 13%, significantly reduced compared to the minimum hunting procedure. However, this is still too large to observe the binding curve for β-lactamase. Denoising the data with singular value decomposition and analysis with the algorithm (a−b)/(a+b) reduces the noise to a level equivalent to minimum hunting (FIG. 6d). The response measured for β-lactamase binding is $(4.05\pm0.15)\times10^{-4}$ (unitless). Hence, denoising the SPR spectra also improves the signal-to-noise ratio of the binding curve with the algorithm (a−b)/(a+b) and results in a relative error of 3.7%. Measurement of a dynamic process results in a similar relative error between the minimum hunting algorithm and the algorithm (a−b)/(a+b). In this case, the relative error is mainly due to the accuracy of the measurement for the binding curve of β-lactamase.

SPR Imaging

Figure 7A:
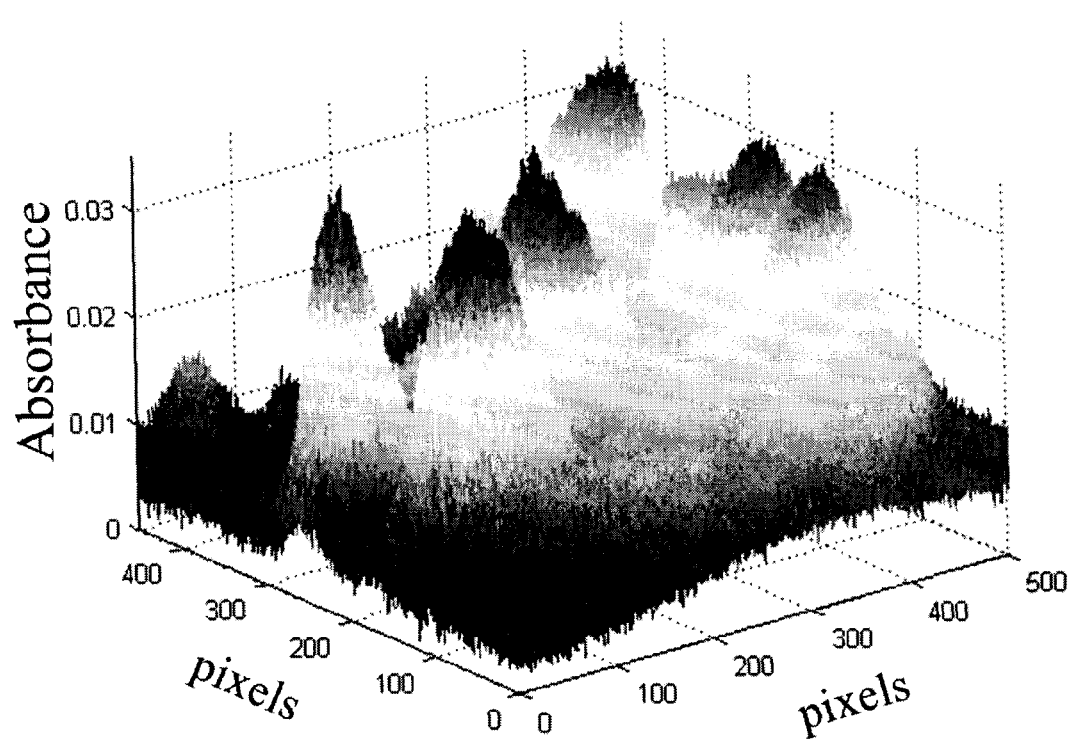
FIG. 7a is a SPR image of water droplets on an Au film obtained from raw data.
Figure 7B:
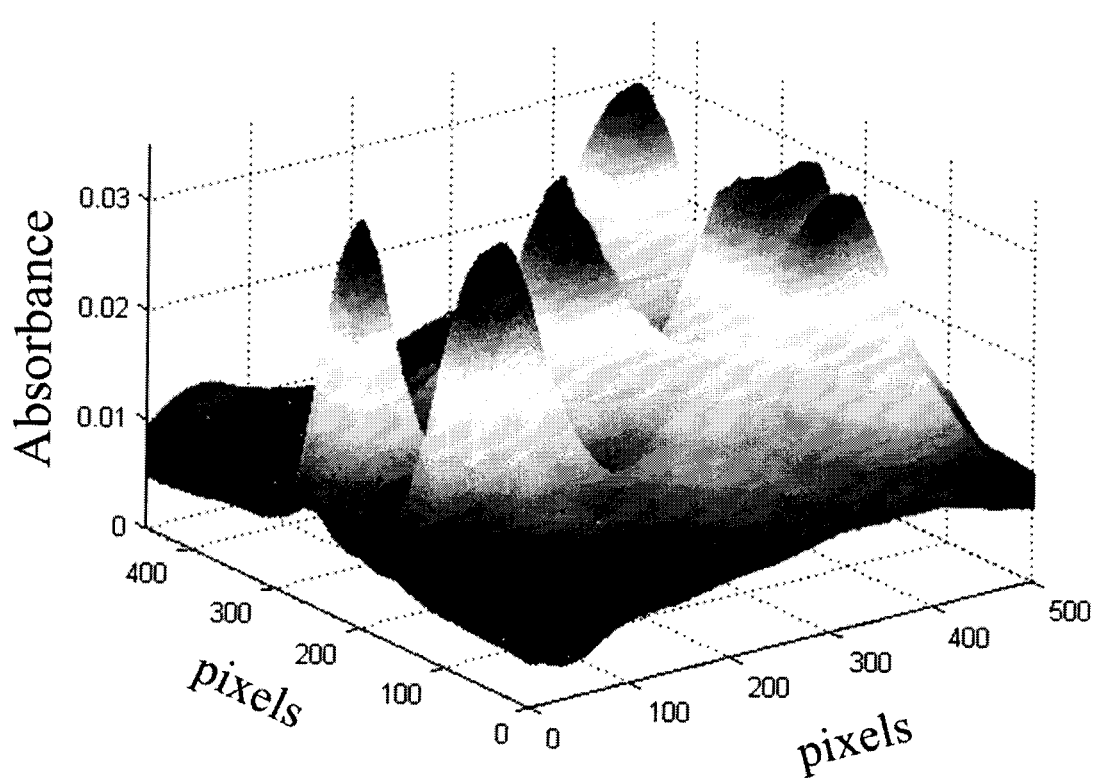
FIG. 7b is a SPR image of water droplets on an Au film obtained from data after denoising with singular value decomposition.

SPR imaging increases in popularity due to the multiplex array format allowing for the analysis of multiple molecules simultaneously in a single sample. The SPR instrument 100 of FIG. 1 using a BK7 dove prism 101 can be readily modified to an imaging configuration with the replacement, as described in the foregoing description, of the collection fiber optic 109/spectrophotometer 113 with a band pass filter/imaging CCD camera. Thus, a 610±10 nm band pass filter (not shown) is mounted between the BK7 dove prism 101 and the imaging CCD camera (not shown). The collimated light beam 114 entering the BK7 dove prism 101 is inverted through the prism with retention of spatial information. Hence, an image of the SPR surface can be obtained with this configuration of the SPR instrument 100. As an example, the SPR image of individual water droplets on the exposed Au surface of the SPR sensor 112 was acquired with this configuration of the SPR instrument 100 (FIGS. 7a and 7b). The image represents an area of approximately 1 cm$^2$. The spatial resolution of the image could be improved using telescopic lenses to zoom on the surface. The absorbance measured for each of the six droplets is constant at 0.0317±0.0012. Denoising the raw data (FIG. 7a) with singular value decomposition reduces significantly the noise on the SPR image (FIG. 7b). In this case, the reconstitution of the SPR image required the use of the first five components to avoid loss of chemical information. With typical SPR spectra (FIGS. 3a-3b and 4), the first three components adequately reconstitute the spectra without loss of chemical information. However, a SPR image requires a larger number of components to adequately reconstitute the image.

The above described SPR instrument 100 can be used to perform biosensing with the SPR multi-wavelength and imaging configurations. The SPR instrument 100 combines low cost and off-the-shelf optical components with high resolution of the measured response. Depending on the data analysis methodology employed to process raw SPR spectra, the resolution varies between $3\times10^{-6}$ RIU and $1.5\times10^{-7}$ RIU. Fitting a second-order polynomial to the SPR spectra results in a resolution lower than using the algorithm (a−b)/(a+b). Denoising the data with singular value decomposition and reconstitution with the components containing the chemical information improves the resolution by approximately one order of magnitude. Therefore, the combination of the algorithm (a−b)/(a+b) and denoising with singular value decomposition increases the resolution. Depending on the spectrophotometer being used, the refractive index accessible ranges from 1.33 to 1.39 RIU with a 550-850 nm spectrophotometer and from 1.33 to 1.42 RIU with a 550-1100 nm spectrophotometer. The measurement of repeated injection of PBS is demonstrated with a fluidic cell 201 resulting in a reproducibility of the measurement of <1% with the dove prism SPR instrument 100.

It should be noted that the BK7 dove prism 101 could be replaced by any other suitable prism capable of performing substantially the same function. The same applies to the other components of the SPR instrument 100, the SPR sensor 112 and the fluidic cell 201.

Although the present invention has been described hereinabove with reference to illustrative embodiments thereof, these embodiments can be modified at will, within the scope of the appended claims, without departing from the nature, spirit and scope of the subject invention.

What is claimed is:

1. A surface plasmon resonance instrument, comprising:
   a frame;
   a first lens mounted to the frame for receiving broadband light generated by an external broadband light generator and for collimating the broadband light into a broadband light beam, the first lens aligning the broadband light beam along a first propagation axis;
   a prism removably mounted to the frame, the prism having a first face for receiving and refracting the broadband light beam onto a sensing face of the prism for sensing thereof, the sensing face being parallel to the first propagation axis and configured to receive a metallic film surface plasmon resonance sensor, the sensing face reflecting the broadband light beam via total internal reflection towards a second face of the prism, the second face refracting the broadband light beam outside the prism along a second propagation axis, the first propagation axis and the second propagation axis being aligned and concentric with one another, wherein the sensing face of the prism; and
   a second lens mounted to the frame and aligned with the second propagation axis for receiving the broadband light beam exiting from the prism; and
   an analyzer optically coupled to the second lens for analyzing the broadband light beam exiting of the prism.

2. A surface plasmon resonance instrument as defined in claim 1, wherein the prism is a dove prism, and wherein the sensing face of the prism is a long face of the dove prism.

3. A surface plasmon resonance instrument as defined in claim 1, wherein the analyzer is selected from the group consisting of (a) a spectrophotometer for processing the broadband light beam from the prism and (b) an optical band pass filter for processing the broadband light beam from the prism, and an imaging camera connected to the optical band pass filter.

4. A surface plasmon resonance instrument as defined in claim 1, comprising a polarizer for processing the broadband light beam from the first lens, which propagates through the first face of the prism.

5. A surface plasmon resonance instrument as defined in claim 1, wherein the second lens is optically coupled to the analyzer via a collection fiber optic.

6. A surface plasmon resonance instrument as defined in claim 1, wherein the metallic film surface plasmon resonance sensor comprises a dielectric layer having a surface covered with a metallic film, and wherein the surface plasmon resonance instrument comprises a fluidic cell for contacting a fluid sample to the metallic film, the fluidic cell comprises a body of material having a face with a recess therein, an inlet port and conduit to supply fluid sample to the recess, and an outlet conduit and port to evacuate fluid sample from the recess, and the surface plasmon resonance instrument comprises a pump or a manual sample inlet to inject with a syringe to produce a flow of fluid sample through the inlet port and conduit, the recess, and the outlet conduit and port.

7. A surface plasmon resonance instrument as defined in claim 1, comprising a polarizer for processing the broadband light beam from the first lens, which propagates through the prism, wherein the first lens, the polarizer, the prism, and the second lens are aligned on the first and second propagation axes.

8. A surface plasmon resonance instrument as defined in claim 1, wherein the surface plasmon sensor comprises a glass slide having a non-metallized surface and a surface covered with a metallic film, wherein the non-metallized surface is applied to the face of the prism.

9. A surface plasmon resonance instrument as defined in claim 1, further comprising a splitter splitting the broadband light beam exiting from the second face of the prism into a first broadband light beam and a second broadband light beam, the analyzer being adapted to analyze each one of the first and the second broadband light beam separately.

10. A surface plasmon resonance instrument as defined in claim 9 further comprising a first polarizer being optically coupled to the first broadband light beam to be analyzed as a detection beam by the analyzer, and a second polarizer being optically coupled to the second broadband light beam to be analyzed as a reference beam by the analyzer.

11. A surface plasmon resonance instrument as defined in claim 9, wherein the first and the second broadband light beams are used for measuring two regions of the metallic film.

\* \* \* \* \*